(12) United States Patent
Li et al.

(10) Patent No.: US 12,060,264 B2
(45) Date of Patent: Aug. 13, 2024

(54) SOC PMUT SUITABLE FOR HIGH-DENSITY SYSTEM INTEGRATION, ARRAY CHIP, AND MANUFACTURING METHOD THEREOF

(71) Applicant: NANJING SHENGXI XINYING TECHNOLOGY CO., LTD, Nanjing (CN)

(72) Inventors: Hui Li, San Jose, CA (US); Feng Yin, Palo Alto, CA (US)

(73) Assignee: NANJING SHENGXI XINYING TECHNOLOGY CO., LTD, Nanjing (CN)

( * ) Notice: Subject to any disclaimer, the term of this patent is extended or adjusted under 35 U.S.C. 154(b) by 166 days.

(21) Appl. No.: 17/870,810

(22) Filed: Jul. 21, 2022

(65) Prior Publication Data
US 2023/0060728 A1 Mar. 2, 2023

(30) Foreign Application Priority Data
Aug. 27, 2021 (CN) .......................... 202110991562.7

(51) Int. Cl.
*B81B 7/00* (2006.01)
*B81C 1/00* (2006.01)
*H01L 23/00* (2006.01)

(52) U.S. Cl.
CPC .......... *B81B 7/007* (2013.01); *B81C 1/00301* (2013.01); *H01L 24/08* (2013.01);
(Continued)

(58) Field of Classification Search
CPC ............ B81B 7/007; B81B 2201/0271; B81B 2207/012; B81B 7/008; B81C 1/00301;
(Continued)

(56) References Cited

U.S. PATENT DOCUMENTS

2015/0357375 A1 12/2015 Tsai et al.
2018/0257927 A1 9/2018 Rothberg et al.
(Continued)

FOREIGN PATENT DOCUMENTS

WO    2014014968 A1    1/2014
WO    2017066612 A1    4/2017
(Continued)

*Primary Examiner* — Mamadou L Diallo
(74) *Attorney, Agent, or Firm* — SOROKER AGMON NORDMAN PTE LTD

(57) ABSTRACT

The present invention discloses an SOC PMUT suitable for high-density system integration, an array chip and a manufacturing method thereof. With the SOC PMUT suitable for high-density system integration, vertical stacking and monolithic integration of a SOC PMUT array with CMOS auxiliary circuits is realized by means of direct bonding of active wafers and a vertical multi-channel metal wiring structure; in addition, the extension to the package layer is implemented by means of TSVs, without any bonding mini-pad on the periphery of the array for communication with the CMOS. Thus, the bottleneck of metal interconnections in conventional ultrasonic transducers is overcome, the chip area occupied by metal interconnections in ultrasonic transducers is greatly reduced, the metal wiring length is reduced, thus the resulting adverse effects of an electrical parasitic effect on the performance of the ultrasonic transducer array are reduced.

12 Claims, 26 Drawing Sheets

(52) U.S. Cl.
CPC ...... *H01L 24/80* (2013.01); *B81B 2201/0271* (2013.01); *B81B 2207/012* (2013.01); *B81B 2207/07* (2013.01); *B81C 2203/0785* (2013.01); *H01L 2224/08145* (2013.01); *H01L 2224/80895* (2013.01); *H01L 2224/80896* (2013.01); *H01L 2924/1461* (2013.01)

(58) Field of Classification Search
CPC ......... B81C 1/00246; H01L 2924/1461; H01L 24/08; H01L 24/80; H01L 2224/08145; H01L 2224/80895; H01L 21/76898; H01L 2225/06541; H01L 25/0657; H01L 24/94; H10N 30/082; B06B 1/06
See application file for complete search history.

(56) References Cited

U.S. PATENT DOCUMENTS

| | | | |
|---|---|---|---|
| 2018/0312399 A1* | 11/2018 | Singh | B81C 1/00039 |
| 2019/0177160 A1 | 6/2019 | Qian et al. | |
| 2020/0152697 A1* | 5/2020 | Qian | H10N 30/06 |
| 2021/0167056 A1 | 6/2021 | Or-Bach et al. | |
| 2021/0206630 A1* | 7/2021 | Qian | B81B 3/0021 |
| 2022/0328411 A1* | 10/2022 | Or-Bach | H01L 27/092 |

FOREIGN PATENT DOCUMENTS

| | | | |
|---|---|---|---|
| WO | 2017151239 A1 | 9/2017 | |
| WO | 2019066637 A1 | 4/2019 | |

\* cited by examiner (a)

(b)

(c)

(d)

(e)

(f)

(g)

(h)

(a)

(b)

(c)

(d)

(e)

(f)

(g)

SOC PMUT SUITABLE FOR HIGH-DENSITY SYSTEM INTEGRATION, ARRAY CHIP, AND MANUFACTURING METHOD THEREOF

TECHNICAL FIELD

The present invention relates to the technical field of high-density System-On-Chip (SOC) semiconductor transducers, in particular to a new structure integrating a three-dimensional (3D) PMUT architecture and System-On-Chip (SOC) and a processing technique thereof.

BACKGROUND ART

An ultrasonic diagnostic equipment emits ultrasonic waves into human body via its ultrasonic probe, receives, amplifies and processes various information generated by the reflection, refraction and diffraction of sound during the propagation of the ultrasonic waves in human organs and tissues to form images or a blood flow Doppler spectrum, and finally displays the images or the blood flow Doppler spectrum on a display unit. A medical color ultrasonic diagnostic equipment mainly comprises a probe, a host, a control panel, a display unit and other accessories.

As the human society enters a Big Medical era, the application of medical ultrasound has been developed rapidly. Ultrasound scanning has spread all over the world, from medical imaging such as fetal B-scan ultrasonography to liver scanning and kidney scanning. Compared with other imaging technologies, the ultrasonic imaging technique has the advantages of non-invasion, painlessness, high real-time performance, high safety, and low price, etc., is highly utilized in the prevention, diagnosis and treatment of patients, and is widely applied in various clinical examinations in gastroenterology department, gynecology department, obstetrics department, urology department, chest department, small organs department, pediatrics department, cardiology department, and emergency department, etc. In addition, the ultrasonic imaging technique has been gradually combined with other clinical departments, and various examination applications have been developed from it, such as endoscopic ultrasonography in gastroenterology department and intravascular ultrasonography in cardiac surgery department, etc. Ultrasonic imaging technique has become an indispensable inspection method at present.

The ultrasonic technique and related products are being introduced into people's daily life rapidly. Smartphone is one of the important applications. The fingerprint identification on smartphones is not only fast and convenient, but also greatly improves the security for the users. Owing to the fact that an ultrasonic transducer has a wide viewing field, it can still achieve accurate range measurement even if it is installed at the top or the bottom of a cell phone. Therefore, the optical proximity transducer on the front of the cell phone can be omitted in the design of the cell phone, so as to realize a full screen design of the cell phone.

After an ultrasonic ranging transducer is installed in a car, the car can keep an appropriate safety distance during driving, reversing and parking, and is very convenient. Moreover, MEMS ultrasonic transducers have been introduced in the application fields such as unmanned aerial vehicles and robots, etc. In such applications, the miniature ultrasonic transducers can accurately keep track of a target, form an array space radar, monitor the movement, position and motion change of human body in real time, and seamlessly connect with VR/AR.

Ultrasonic transducers are also widely applied in industrial control. For example, they can detect the shape change of aircraft wing surfaces, detect icing, and thereby ensure flight safety. Ultrasonic transducers installed on an aircraft engine can detect any fracture in the engine in real time, and find out problems in time for reparation or replacement.

A conventional ultrasonic probe is produced from a piezoelectric ceramic crystal through mechanical cutting, arrangement, and metal interconnecting and wiring. Firstly, a piece of piezoelectric ceramic crystal is taken to be fixed on a supporting substrate, and then mechanical cutting is carried out in X direction and Y direction. However, with such a processing method, the yield is low, mechanical damages may occur easily, it is difficult to control the cost and realize mass production. More importantly, the machining accuracy is low, the minimum size of the finished crystal is limited, and the requirement of high-resolution medical imaging for PMUT's gradual size decrease can't be met.

The CMOS-based Micro Electrical-Mechanical System (MEMS) technique has been received great attention and regarded as the developing trend of ultrasonic transducers. Semiconductor MEMS ultrasonic transducers are the most promising technique for realizing high-resolution medical ultrasonic array transducers, thanks to the high precision and high yield of the CMOS process. However, at present, the CMOS-based MEMS technique is a planar technique. As the density of the ultrasonic transducer array increases, length and density of metal lead wires required for the interconnections between the units and the interconnections between the units and the external devices increase rapidly, and the chip area occupied by the lead wires even far exceeds the chip area occupied by the transducer array, leading to rapid increase of the size of the packaged circuits and system. In addition, with the increase of the metal lead wires, in conjunction with the side effects such as the resistance of the metal lead wires and capacitive delay effect, the voltage drop, and the electrical interference incurred by the coupling between the metal lead wires, the working performance of the transducer is affected adversely, and the adverse effect become more and more serious with the increase of the array density.

However, the normal operation of the PMUT requires the support of many auxiliary circuits. FIG. 1 is a block circuit diagram of a typical PMUT system. It can be seen that the PMUT requires a high-voltage (usually 10 to 25 V) pulsed driving circuit to work. A high-voltage source circuit generates and outputs high direct current (DC) voltage, the high DC voltage is converted into a specific pulsed driving signal by a pulse modulation circuit, and ultrasonic waves at a specific frequency are generated by a PMUT array based on the pulsed driving signal and then are emitted. That process is the ultrasonic wave emission process.

When the ultrasonic waves are reflected back by scanned objects such as different organs of a human, the PMUT receives the ultrasonic waves and convert the ultrasonic waves into electrical signals through a piezoelectric effect, then inputs the electrical signals to a low-noise signal amplifier and then to a variable gain control circuit for signal amplification; then the analog signals are converted by an analog/digital converter circuit into digital signals, then the digital signals are outputted to a microprocessor, and an ultrasonic image is formed by the ultrasonic imaging algorithm.

The PMUT requires multiple CMOS analog and digital circuits to cooperate with it, regardless of whether it is in an ultrasonic wave emission mode or an ultrasonic wave receiving mode. If all of the different circuits in the block circuit diagram of a PMUT system are formed by discrete IC packaged circuit blocks, multiple IC blocks are required to implement the system, and the multiple IC blocks need to be bonded on a printed circuit board (PCB) so as to be interconnecting. Consequently, the system has a considerable size. The large size may not be a problem for a large-size ultrasonic system, such as a floor-standing ultrasonic scanner. However, nowadays, the voice for miniaturized ultrasonic scanners or even portable ultrasonic scanners becomes stronger increasingly, and ultrasonic scanners must have a reduced size. Such a planar architecture can't meet the requirement anymore.

MEMS-on-CMOS is a semiconductor transducer technique that arranges Micro Electrical-Mechanical System (MEMS) transducers on top of a CMOS chip to realize a high-density System-On-Chip (SOC). The Piezoelectric Micromachined Ultrasonic Transducer (PMUT) technique, like other MEMS techniques, is intended to improve the level of integration with the help of the PMUT-on-CMOS technique path to provide high-density PMUT arrays for applications such as high-resolution ultrasonic scanning and ultrasonic fingerprint identification, etc.

The PMUT-on-CMOS technique, as shown in FIG. 2(a), can stack two original chips vertically by means of System-On-Chip, and thereby reduces the planar dimensions, the number of packaged ICs, and the size of the system.

However, up to now, this seemingly direct and reasonable solution has not been adopted widely, mainly because that some new technical challenges will be encountered to realize PMUT-on-CMOS in the existing planar process architecture.

Firstly, in the prior art, a PMUT array has to be interconnected with the CMOS circuit below via peripheral bonding pads (or mini-pads). As a result, the metal wiring faces two major limitations. First, if it is desired that each unit has its own independent top-layer metal connection, as shown in FIG. 2(b), additional metal wiring is required. Consequently, the duty ratio of the PMUT unit (i.e., a ratio of the area where ultrasound can be generated to the area of the entire unit) is decreased by the metal wiring; besides, the metal wiring occupies a great proportion of the chip area outside the array, and the parasitic resistance and capacitance produced by additional metal wiring have adverse effects on the speed and power consumption, etc. Second, at present, in the designs of most PMUT arrays, multiple units in the same column share the same metal wiring in the top layer (common column connection) in order to reduce additional metal wiring; consequently, the cross-talk among the units become serious, and the main performance parameters of the PMUT array, such as effective frequency bandwidth and signal-to-noise ratio (SNR), etc., are affected adversely.

Secondly, to build PMUTs on CMOS, the choice of the material and the manufacturing process are constrained to some extent. For example, considered from the mechanical properties, repeatability and uniformity of the material, silicon is a good material for the mechanical substrate layer for PMUT. However, owing to the limitation of the growth conditions (for example, the temperature of the silicon epitaxy is above 1,000° C.) of the silicon material above CMOS ICs, there is no way to form a monocrystalline silicon mechanical layer on a CMOS wafer.

The demand for high-end development of ultrasonic products is endless. Medical ultrasonic imaging requires increasingly greater PMUT arrays to achieve higher definition; fingerprint identification imaging requires more and more PMUT units to achieve higher resolutions. However, unfortunately, the present PMUT techniques have encountered a bottle neck on the road of continuous miniaturization and require technical breakthroughs.

The most commonly used materials for PMUT thin film piezoelectric ultrasonic transducers are AlN (aluminum nitride) and PZT (lead zirconate titanate, Pb(ZrTi)O$_3$, PZT for short). Compared with the standard CMOS process, these materials and processes are quite different. For example, for the PZT material, special deposition equipment and etching and cleaning equipment that are different from those for the CMOS process are required, which require considerable investment. Besides, the PZT material causes metal contamination to the CMOS process, which affects the performance and reliability of CMOS products. Therefore, there are only a few PMUT production lines in the world. To make high-performance and low-cost ultrasonic transducers by adding a PMUT process based on the CMOS process, persistent innovations and renovations are required in component structure, process flow and system design. Similar to the PZT material, special equipment and additional investment are also required for the AlN (aluminum nitride) piezoelectric material.

The structure of a typical PMUT piezoelectric ultrasonic transducers 100 is shown in FIG. 3, comprising:

a substrate material 160, which usually may be a silicon material or silicon dioxide material, wherein the silicon dioxide is usually also deposited on the silicon substrate;

a cavity 120, which is usually formed by etching in the substrate material to leave room for the PMUT to vibrate mechanically up and down and emit or receive ultrasonic waves;

a mechanical layer 130, which serves as a mechanical support for the vibrating PMUT film to ensure the service life of the PMUT; the properties of the material of the mechanical layer 130 such as thickness, specific gravity, and Young's modulus, etc. also have an influence on the vibration frequency of the PMUT;

an oxide layer 132, which is usually a silicon dioxide layer produced on the silicon surface in the CMOS process; the oxide layer 132 has a protective function for the silicon surface, and the thickness of the oxide layer 132 has an influence on the vibration frequency of the PMUT.

The sandwiched stack structure of the piezoelectric layer includes a piezoelectric material layer 115, and associated electrode layers arranged under the piezoelectric material layer 115 and above the piezoelectric material layer 115, which are a bottom electrode 112 and a top electrode 114 respectively.

The most commonly used materials for the piezoelectric material layer 115 are PZT lead zirconate titanate (Pb(ZrTi)O$_3$, PZT for short) and AlN (aluminum nitride).

The bottom electrode 112 and the top electrode 114 corresponding to PZT are usually platinum (Pt) material or have a multi-layer structure formed by platinum (Pt) and titanium (Ti) metal materials. The bottom electrode 112 and the top electrode 114 corresponding to AlN are usually made of molybdenum. A voltage is applied between the bottom electrode 112 and the top electrode 114 to generate an electric field in the piezoelectric material, thereby the piezoelectric material expands and retracts, and produces mechanical vibrations in the vertical direction, so that ultrasonic waves are emitted. That is the well-known piezoelectric effect.

The frequency of the mechanical vibrations of PMUT is related with the properties of the materials of the layers in the sandwiched stack structure of the piezoelectric layer, the properties of the materials in the mechanical layer 130 and the oxide layer 132, the thickness of all materials, and the shape and size of the cavity 120. The mechanical stresses in all material also have an influence on the vibration frequency.

A high-resolution and high-integration medical PMUT ultrasonic probe requires 10 to 50 MHz high frequency. The requirements for the sizes and accuracies of different structures in the PMUT structure 100 are very high. For example, the control of the size of the cavity 120 and the range of size change of the cavity 120 has direct influence on the key parameters of the ultrasonic probe, such as working frequency and working bandwidth, etc. With the commonly used method of etching the wafer from the back side to form the structure of a cavity 120 at present, the structural dimension variation of the cavity 120 may be 5 to 10 μm or even greater. Consequently, the requirement for high frequency and high resolution can't be met at all. Besides, with the method of etching the wafer from the back side to form the structure of a cavity 120, it is difficult to form cavities 120 with different structural dimensions at the same time. Consequently, the possibility of producing single-chip multi-frequency ultrasonic probes is limited, resulting in a severe limitation on the application.

Similar to the requirement for controlling the size of the cavity 120 and the dimension change range of the cavity 120, the film thickness and the control therefor in the PMUT piezoelectric ultrasonic transducers structure 100 is also critical. For example, the film thickness and control, the specific gravity and Young's modulus of the materials, and even the mechanical stress in the materials in the piezoelectric material layer 115, the mechanical layer 130, the bottom electrode 112 and the top electrode 114, etc. have direct influences on the key parameters of the ultrasonic probe, including working frequency, working bandwidth, ultrasonic wave output power, and electromechanical coupling factor, etc.

In the existing PMUT array techniques and product applications, it is a great challenge to realize the electrical connection between the PMUT and the peripheral circuits and systems, regardless of whether a crystal cutting method or a MEMS semiconductor IC method is used. FIG. 4 is a top view of a typical PMUT array chip. A 7×12 two-dimensional array of PMUTs is located at the center of the chip, and mini-pads are located on the periphery of the chip to establish electrical connections with the pins of the circuit package. Since each PMUT unit in the array has to be connected to the mini-pads and there are design requirements for the lead width and lead spacing of the metal wiring for electrical connections, actually most of the chip area is used for the metal wiring. The chip area occupied by the metal wiring is much greater than the chip area occupied by the PMUT array, which is very wasteful. In addition, the great metal wiring length causes an increased parasitic effect of resistance and capacitance, and has adverse effects on the working frequency and power consumption of the PMUT array. The uneven wiring lengths also have a direct influence on the operating uniformity of the PMUT array.

SUMMARY OF THE INVENTION

In order to overcome the above-mentioned drawbacks in the interconnections in existing ultrasonic transducers, the present invention proposes an ultrasonic transducer with a ground-breaking 3D architecture and a process thereof. In the ultrasonic transducer proposed by the present invention, a PMUT array, high-voltage driving and control CMOS circuits for the ultrasonic transducer, and a low noise amplifier circuit for ultrasonic wave receiving. etc. are stacked vertically, and then connected together through vertical lead vias, without any bonding mini-pad on the periphery of the PMUT array for communication between the PMUT units and the CMOS units. Thus, the bottleneck of metal interconnections in conventional ultrasonic transducers is overcome, the ultrasonic transducer array is greatly miniaturized, and the level of chip integration is improved remarkably.

To attain the above-mentioned object, the present invention provides a SOC PMUT architecture suitable for high-density system integration, in which a PMUT array is stacked on top of CMOS unit; the PMUT is connected with the CMOS through vertical link vias rather than peripheral bonding mini-pads; the CMOS is no longer a single-layer planar CMOS; instead, two wafers with preformed CMOS are stacked together by a hybrid bonding method, thereby the integration density is doubled; the components are connected to a printed circuit board (PCB) on the back side of the chip through TSVs.

In the embodiments of the present invention, a SOC PMUT suitable for high-density system integration is provided, comprising: a first wafer and a second wafer, wherein a silicon substrate is arranged on the first wafer, at least one CMOS unit is arranged above the silicon substrate, and a metal interconnect layer of the at least one CMOS unit is vertically interconnected with a second metal wiring layer above the metal interconnect layer through metal lead vias; Through-Silicon Vias (TSVs) are arranged in the silicon substrate for vertically interconnecting the metal interconnect layer with the back side of the silicon substrate; the first wafer and the second wafer are stacked by hybrid bonding, and the first wafer and the second wafer are electrically interconnected by bonding metal mini-pads arranged on hybrid bonding interfaces of the two wafers; the bonding metal mini-pads arranged on the hybrid bonding interface of the first wafer are electrically interconnected with the second metal wiring layer; a mechanical layer of the SOC PMUT is arranged on the second wafer, at least one cavity is arranged under the mechanical layer, at least one CMOS auxiliary circuit for supporting the operation of the SOC PMUT is arranged in the mechanical layer, and a metal interconnect layer of the CMOS auxiliary circuit is vertically interconnected with a second layer of metal under the metal interconnect layer through metal interconnection vias; the second layer of metal is electrically interconnected with the hybrid bonding mini-pads arranged on the hybrid bonding interface of the second wafer; a bottom metal layer, a piezoelectric material layer and a top metal layer of the SOC PMUT are arranged above the mechanical layer, the metal interconnect layer 301 of the CMOS auxiliary circuit is vertically interconnected with the top metal layer through top metal link vias ZTMs, and is vertically interconnected with the bottom metal layer through bottom metal link vias ZBMs.

In the embodiments of the present invention, an array chip is provided, comprising a plurality of SOC PMUTs suitable for high-density system integration, wherein the plurality of SOC PMUTs vertically connect the top metal layer to the CMOS auxiliary circuit through the top metal link vias ZTMs respectively, then vertically connect to the second layer of metal of the second wafer through the metal interconnection vias, then vertically connect to the second layer of metal wiring of the first wafer through the hybrid bonding mini-pads arranged on the hybrid bonding interfaces of the two wafers, then vertically connect to the metal interconnect layer of the CMOS unit through the two metal lead vias respectively, and then lead to the back side of the silicon chip through the TSVs and connect to a printed circuit board respectively.

Preferably, the mechanical layer is made of the same material as the silicon substrate.

Preferably, a metal structure of stop layer is arranged in the bottom layer of the mechanical layer, and the top metal link vias ZTMs and the bottom metal link vias ZBMs are electrically interconnected with the metal interconnect layer of the CMOS auxiliary circuit through the metal structure of stop layer.

Preferably, at least one layer of metal wiring is further arranged above the second layer of metal wiring in the substrate material, and each layer of metal wiring in the at least one layer of metal wiring is vertically interconnected through metal lead vias, the bottommost layer of metal wiring in the at least one layer of metal wiring is vertically interconnected with the second layer of metal wiring through metal lead vias, and the topmost layer of metal wiring in the at least one layer of metal wiring is electrically interconnected with the bonding metal mini-pads arranged on the hybrid bonding interface of the first wafer.

In the embodiments of the present invention, a manufacturing method of the SOC PMUT suitable for high-density system integration is further provided, comprising the following steps:

step 1: preparing a first wafer, growing silicon dioxide on the surface of the first wafer, and manufacturing CMOS unit:

step 2: manufacturing PMUT unit on top of the CMOS unit and integrating CMOS auxiliary circuit, specifically comprising:

step 2-1: depositing a substrate material at a low temperature, and chemically and mechanically polishing the substrate material to form a flat surface of the substrate material; step 2-2: performing photolithography and etching and metal deposition and filling to form metal lead vias between a metal interconnection layer of the MOS circuit unit and a second layer of metal wiring;

step 2-3: depositing a metal layer, performing photolithography and etching to form a second layer of metal wiring, removing the photoresist and cleaning:

step 2-4: depositing a substrate material at a low temperature, and chemically and mechanically polishing the substrate material to form a flat surface of the substrate material; step 2-5: performing photolithography and etching to form a cavity, removing the photoresist and cleaning;

step 2-6: preparing a second wafer, growing silicon dioxide on the surface of the second wafer, manufacturing required CMOS auxiliary circuit, and bonding the second wafer to the first wafer;

step 2-7: grinding the back side of the second wafer, etching the back side with a chemical liquid, and reducing the thickness of the second wafer by chemical and mechanical polishing;

step 2-8: performing metal deposition to form a bottom metal layer;

step 2-9: depositing a piezoelectric material to form a piezoelectric material layer;

step 2-10: depositing a metal material on the top layer and performing photolithography and etching to form a top metal layer;

step 2-11: performing photolithography and etching, and metal deposition and filling to form metal link vias;

step 2-12: performing metal photolithography and etching to form required wiring;

step 3: performing photolithography and etching through the back side of the silicon substrate and performing metal deposition to form TSVs (Through Silicon Vias).

Beneficial Effects

In the design and manufacturing process of existing 2D planar ultrasonic transducer arrays, the chip area occupied by the metal wiring is much greater than the chip area occupied by the ultrasonic transducer array, which is very wasteful. In addition, the long wiring has adverse effects on the working frequency, power consumption, heat dissipation, and other important indexes of an ultrasonic transducer, and the uneven wiring lengths also have a direct influence on the operating uniformity of the ultrasonic transducer array. With the ultrasonic transducer proposed by the present invention, metal interconnections in the three-dimensional structure of the ultrasonic transducer and the CMOS unit are realized by means of a vertical multi-channel metal wiring structure, and extension to the package layer is implemented through Through-Silicon Vias (TSVs), without any bonding mini-pad on the periphery of the array for communication with the CMOS. Thus, the bottleneck of metal interconnections in conventional ultrasonic transducers is overcome, the chip area occupied by the metal interconnection is greatly reduced, the metal wiring length is reduced by 10 to 100 times, thus the resulting adverse effects of an electrical parasitic effect on the performance of the ultrasonic transducer array are reduced.

An ultrasonic transducer array requires the support of CMOS auxiliary circuits, such as pulse signal generation and control circuit and small signal amplifier analog circuits, etc., to operate. At present, all of those auxiliary circuits are packaged in discrete packages, which occupy a large area of the printed circuit board (PCB). If some or all of those circuits are integrated into the ultrasonic transducer chip, the level of system integration can be greatly improved, which is of great significance for reducing the size of the system and realizing the miniaturization of ultrasonic scanners. Besides, SOC system integration can greatly improve the system speed and reduce the power consumption.

To that end, in the present invention, the CMOS auxiliary circuits of the ultrasonic transducer array are stacked and integrated from conventional discrete circuits into the 3D architecture of the ultrasonic transducer through 3D vertical interconnection of metal wiring with an active wafer stacking and system integration method, thereby a three-dimensional architecture of System-On-Chip (SOC) ultrasonic transducer is formed, and the system integration is improved from chip level to system level.

The 3D architecture of SOC ultrasonic transducer proposed by the present invention is not only applicable to PMUT but also applicable to CMUT, although the embodiments of the present invention are described in connection with PMUT.

In the 3D architecture of SOC ultrasonic transducer proposed by the present invention, each ultrasonic transducer may have its own top layer and bottom layer metal wiring, and the size and geometric layout of the array may be adjusted according to different applications, thereby the operating flexibility of the ultrasonic transducer array is greatly improved.

The miniaturization of an ultrasonic system requires the miniaturization of the ultrasonic transducer package. In modern semiconductor packaging, Through Silicon Via (TSV) is an effective way for miniaturization of the package size. The compatibility of the 3D architecture with the TSV process is considered fully in the design of the 3D architecture of ultrasonic transducer and the process flow in the present invention.

In the SOC ultrasonic transducer with a 3D architecture proposed by the present invention, vertical stacking and monolithic integration of a SOC PMUT array with CMOS auxiliary circuits is realized by means of direct bonding of active wafers and a vertical multi-channel metal wiring structure, and the extension to the package layer is implemented through TSV, without any bonding mini-pad on the periphery of the array for communication with the CMOS. Thus, the bottleneck of metal interconnections in conventional ultrasonic transducers is overcome, the chip area occupied by the metal interconnections in an ultrasonic transducer is greatly reduced, the metal wiring length is greatly reduced, the chip size and system size are remarkably reduced, and parasitic resistance, capacitance-related power consumption, delay, and the non-uniformity resulted from metal wiring are reduced. The present invention is greatly beneficial for improving the product performance, reducing the product cost, and improving the yield, and can realize chip miniaturization and high-density system integration. The process flow of the ultrasonic transducer with a 3D architecture in the present invention has high compatibility with the main-stream processes for semiconductor, main-stream equipment for semiconductor, and existing chip packaging processes. The present invention can support high-resolution medical ultrasonic planar arrays, realize multi-frequency scanning with a single ultrasonic probe, and is very suitable for high-integration and low-cost commercial applications, such as fingerprint identification on cell phones, etc. The present invention can remarkably reduce the volume of the chip and package system, and is suitable for the designs of small-sized ultrasonic probes that are led into human body.

DETAILED DESCRIPTION

Hereunder taking PMUT as an example, the technical solution of the present invention will be further described in detailed with reference to specific embodiments.

Example 1

Figure 1:
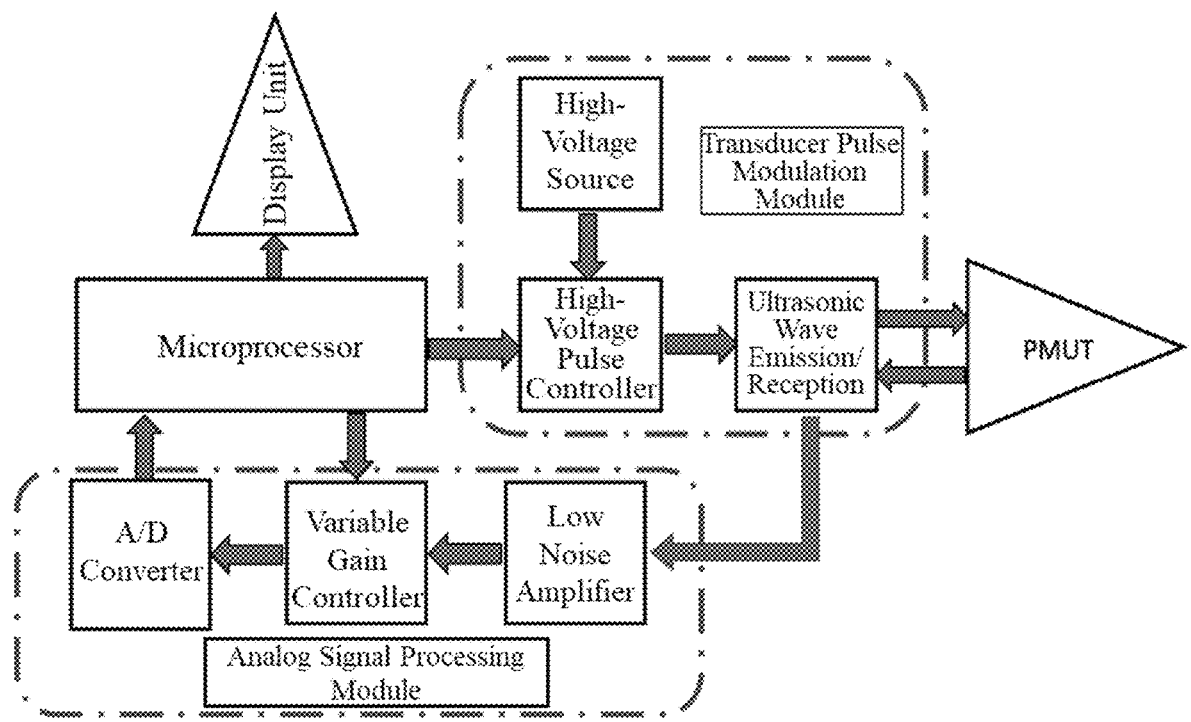
FIG. 1 is a block circuit diagram of a PMUT system.
Figure 2A:
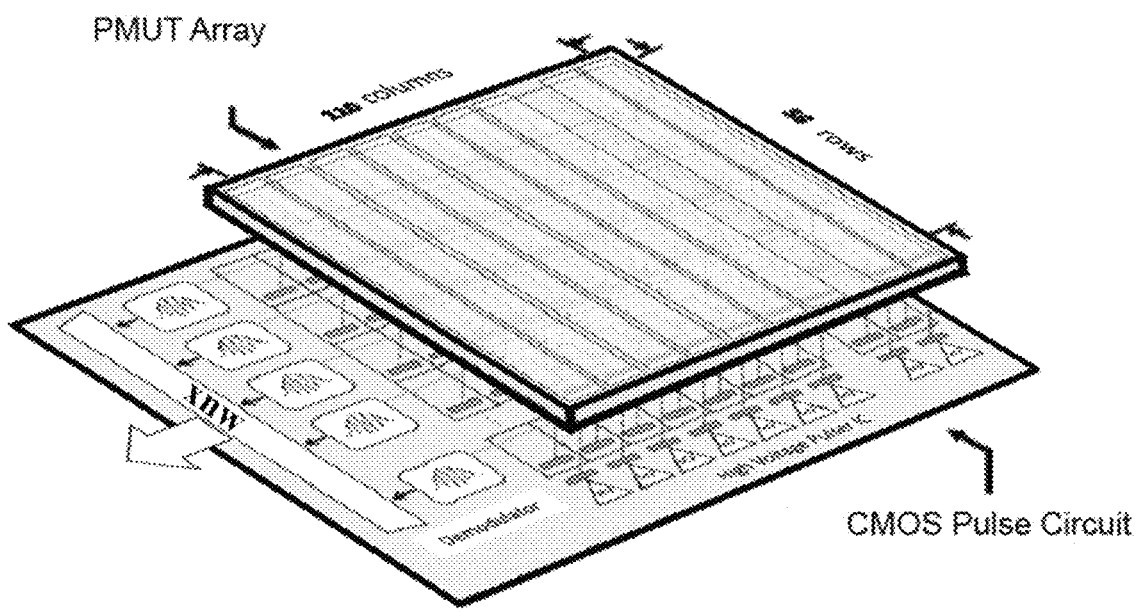
FIG. 2(a) shows the existing PMUT-on-CMOS architecture.
Figure 2B:
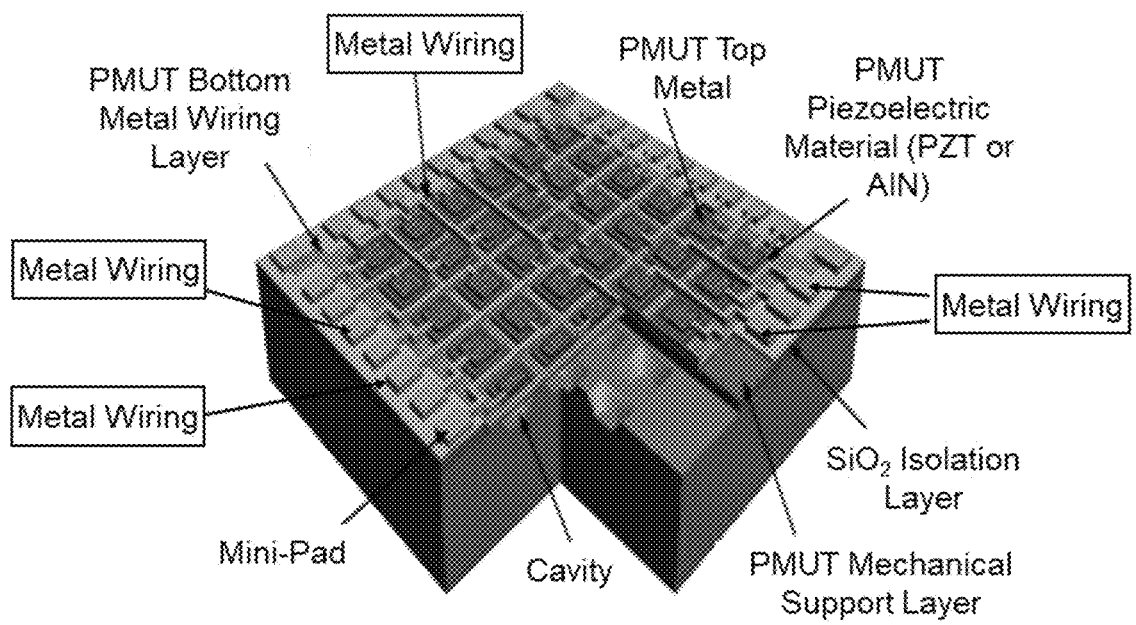
FIG. 2(b) is a schematic diagram of the metal wiring connection in the existing PMUT-on-CMOS architecture.
Figure 3:
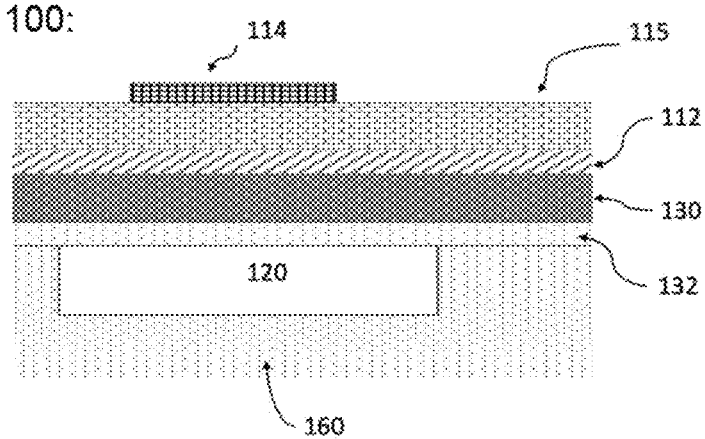
FIG. 3 is a schematic structural diagram of an existing 2D PMUT.
Figure 4A:
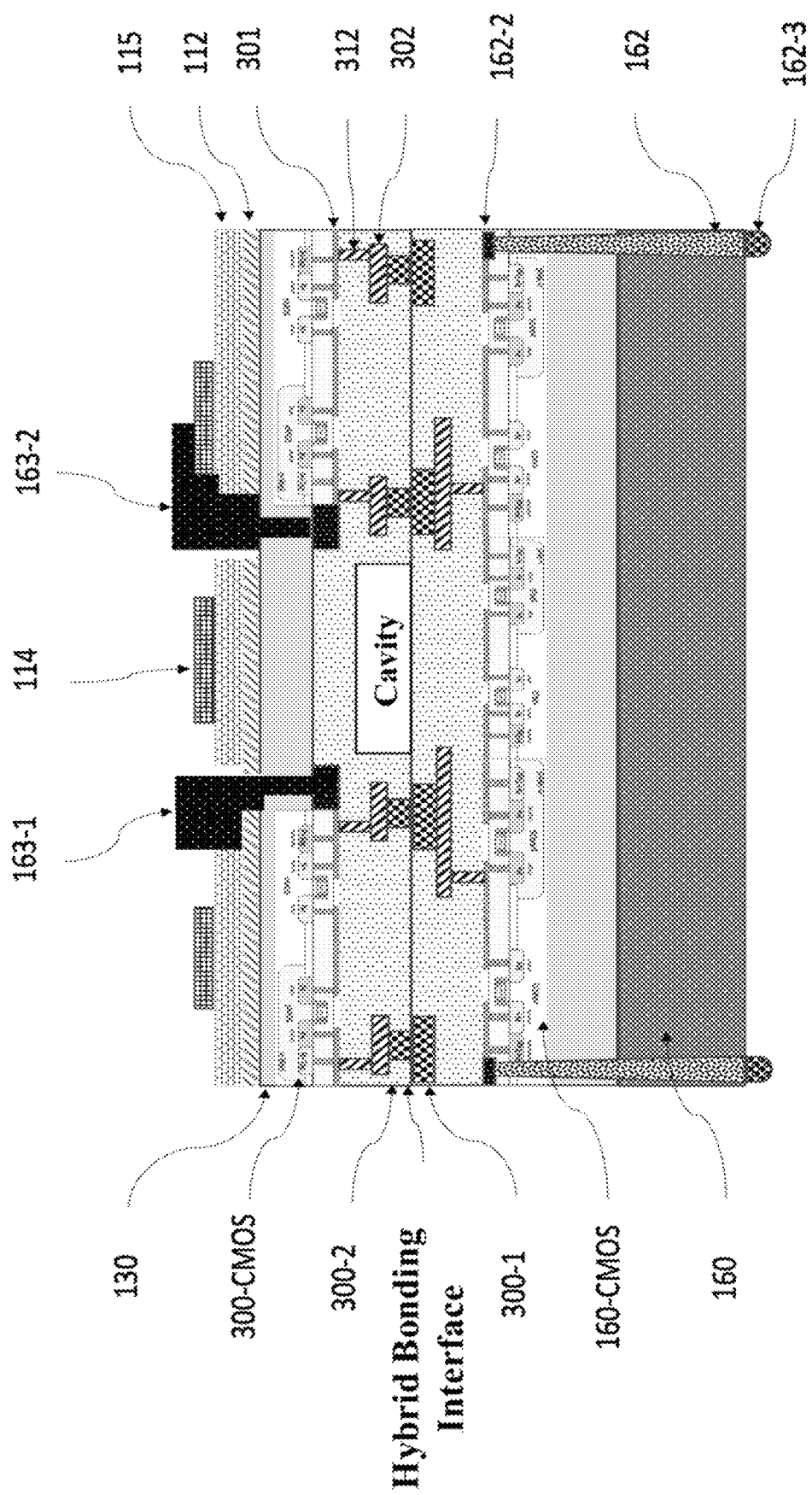
FIG. 4(a) is a schematic structural diagram of the PMUT in the example 1 of the present invention.
Figure 4B:
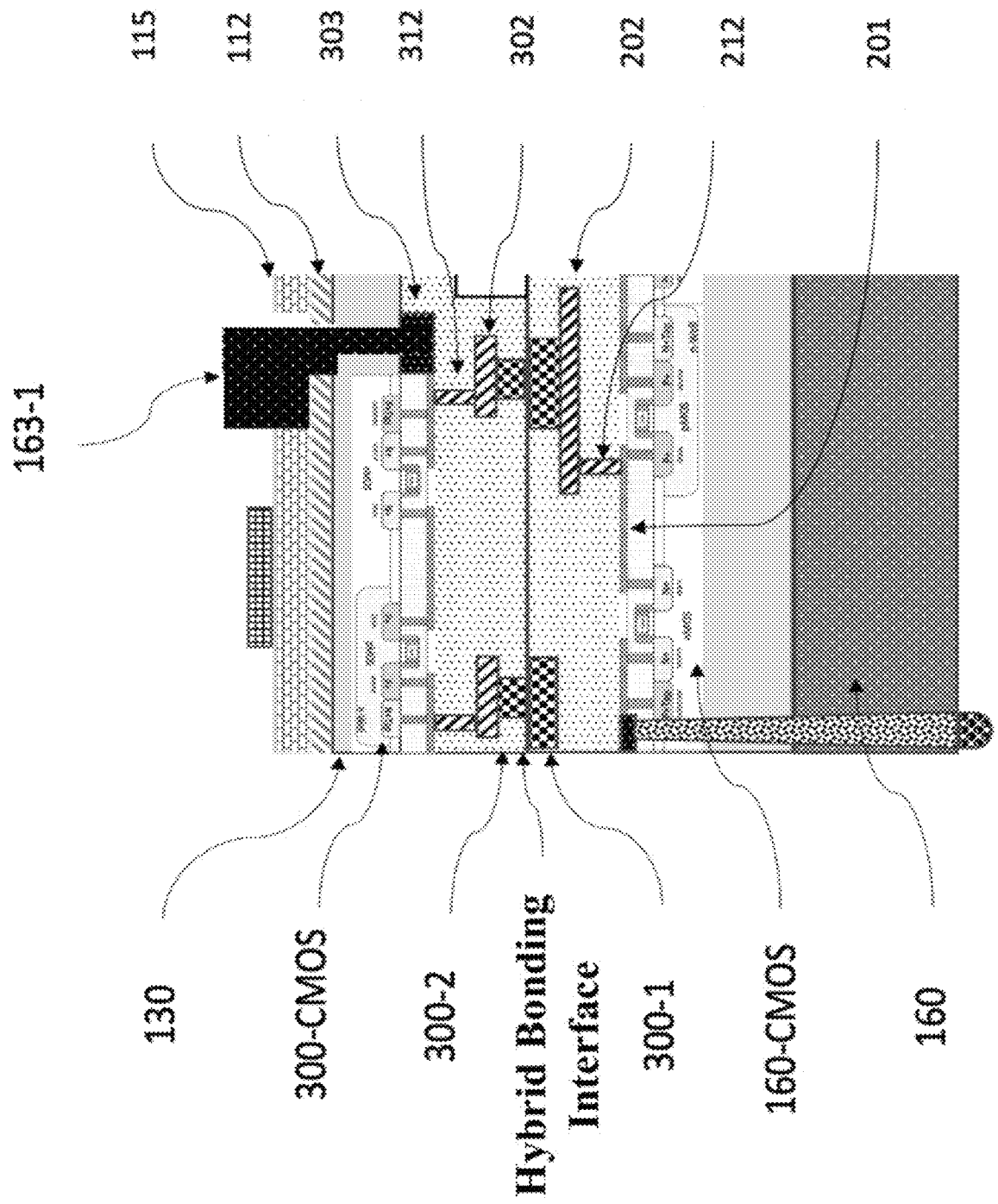
FIG. 4(b) is a schematic diagram of the partial structure of the PMUT in the example 1 of the present invention.
Figure 4C:
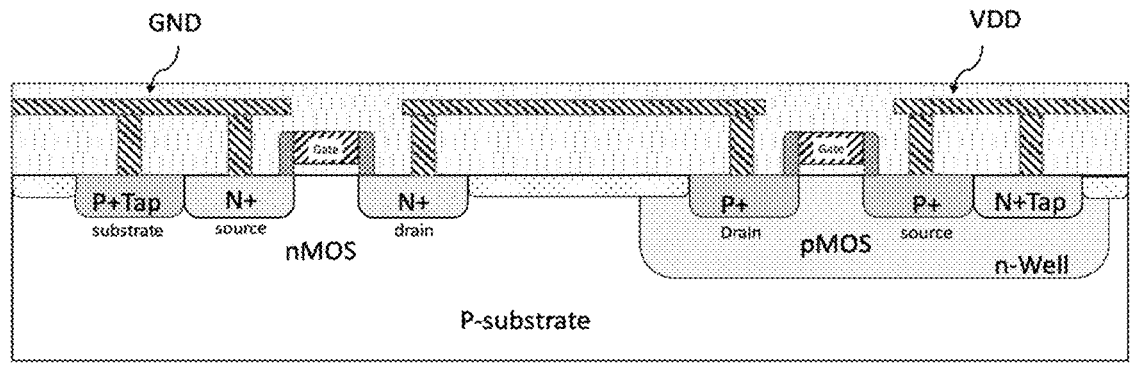
FIG. 4(c) is a schematic structural diagram of a CMOS device according to an embodiment of the present invention.

As shown in FIGS. 4(a) and 4(b), in this example, a SOC PMUT suitable for high-density system integration is provided. The SOC PMUT comprises a first wafer and a second wafer, wherein a silicon substrate material 160 and a CMOS unit 160-CMOS with metal wiring in double-layer are arranged in the first wafer, a mechanical layer 130, a bottom metal layer 112, a piezoelectric material layer 115, a top metal layer 114, a cavity 120, and CMOS auxiliary circuit 300-CMOS with metal wiring in double-layer are arranged in the second wafer.

Figure 25:
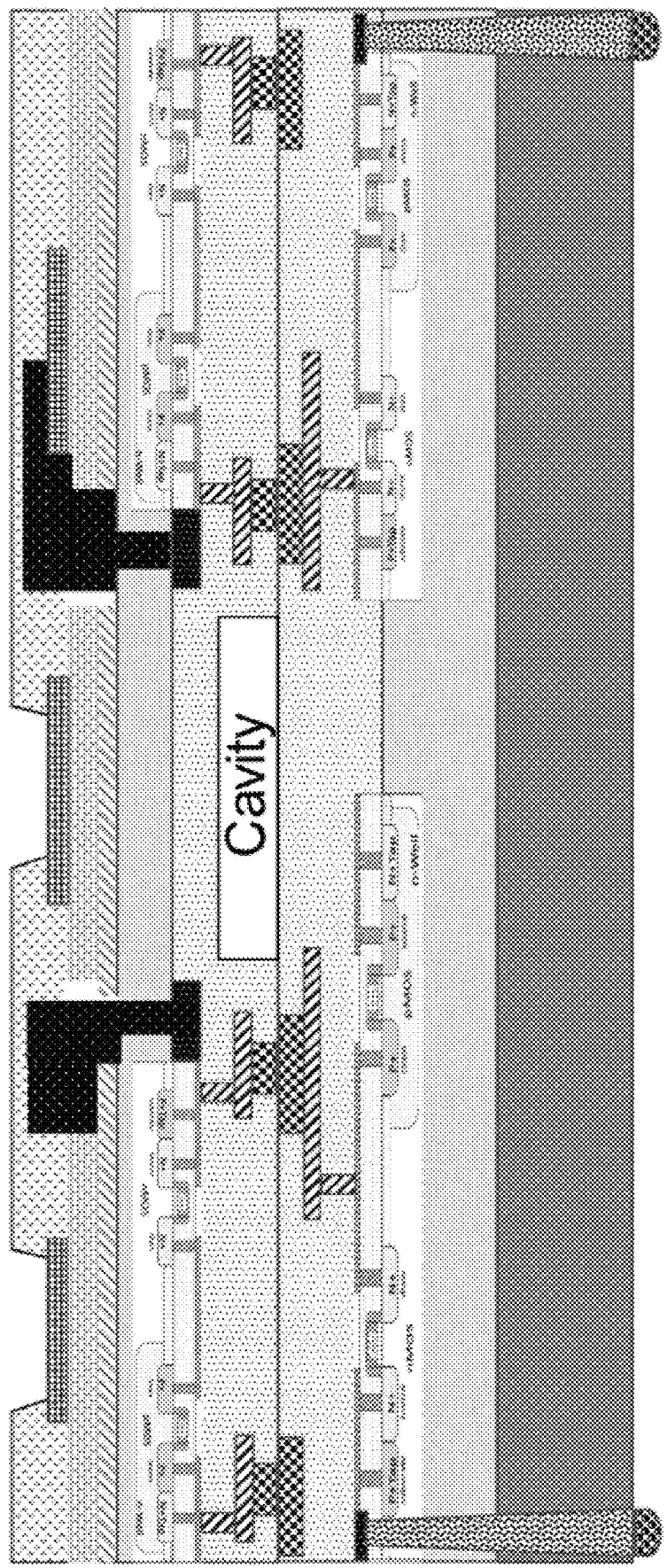
FIG. 25 is a schematic diagram showing that Through-Silicon Vias are formed in step 3 of the example 4 of the present invention.
Figure 26:
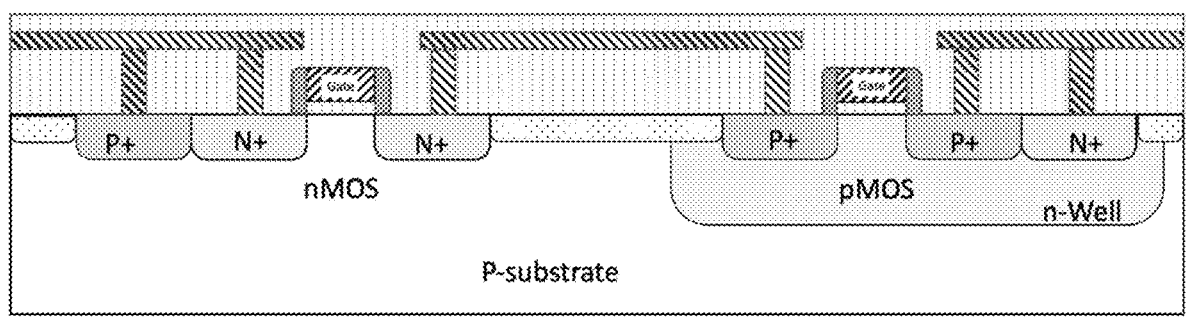
FIG. 26 is an enlarged schematic diagram of the CMOS unit in the embodiments of the present invention.

The two ends of a metal interconnect layer 201 for the CMOS unit 160-CMOS arranged above the silicon substrate 160 are vertically interconnected with two second layer of metal wirings 202 above the metal interconnect layer 201 through two metal lead vias 212 respectively. Two Through-Silicon Vias (TSVs) 162 penetrating through the entire silicon substrate 160 are arranged in the silicon substrate 160, so as to vertically interconnect the two ends of the metal interconnect layer 201 of the CMOS unit to the back side of the silicon substrate 160 respectively, specifically to the TSV welding balls 163-3 on the back side, and then to the printed circuit board directly. The structure of the CMOS unit 160-CMOS is shown in FIG. 25, and belongs to the prior art in the technical field.

The mechanical layer 130 is integrated with a SOC CMOS circuit, i.e., CMOS auxiliary circuit 300-CMOS. The electrically interconnections between the CMOS auxiliary circuit 300-CMOS and other structures are implemented by a metal interconnect layer 301 for the CMOS auxiliary circuit (i.e., the first layer of metal wiring in the metal wirings in double-layer for the CMOS auxiliary circuits), a second layer of metal 302 (i.e., the second layer of metal wiring in the metal wirings in double-layer for the CMOS auxiliary circuits), and metal interconnection vias 312, and are all connected to the etch-stop 303 of vertical lead vias. The structure of the CMOS auxiliary circuit 300-CMOS is designed according to the specific circuit requirements, and the basic structure of the CMOS auxiliary circuits 300-CMOS is similar to the structure of the CMOS unit 160-CMOS.

The bonding metal mini-pads 300-1 and 300-2 are arranged on the hybrid bonding interfaces of the two wafers respectively, the bonding metal mini-pads 300-1 on the hybrid bonding interface of the first wafer are connected to the second layer of metal wiring 202, the bonding metal mini-pads on the hybrid bonding interface of the second wafer are connected to the second layer of metal 302 of the CMOS auxiliary circuit at one side of the mechanical layer, and finally connected to metal link vias 163-1 and 163-2 of the PMUT array.

The top metal link vias ZTMs 163-1 and the bottom metal link vias ZBMs 163-2 penetrate through the piezoelectric material layer 115, the bottom metal layer 112, the mechanical layer 130 and the oxide layer 132, and are both connected to the metal structure of stop layer 303. The metal structure of stop layer 303 is the etch-stop metal that is utilized when the vertical lead vias 163-1 and 163-2 are etched, and the material of the metal structure of stop layer 303 is the same as the metal material of the metal interconnect layer 301 for the CMOS auxiliary circuit. The top metal link vias ZTMs 163-1 implement the vertical interconnections between the top metal layer 114 of the PMUT and the metal structure of stop layer 303 and the CMOS auxiliary circuit 300-CMOS, and the bottom metal link vias ZBMs 163-2 implement the vertical interconnections between the bottom metal layer 112 and the metal structure of stop layer 303 and the CMOS auxiliary circuit 300-CMOS.

Since the top metal link via ZTMs and the bottom metal link via ZBMs pass through top PMUT metal layer (TM) that are different in height and piezoelectric material (PZT) and then are vertically connected, they have an essentially Z-shaped cross section, therefore are referred to as Z-shaped vias. A Z-shaped via can implement an electrical connection with more than two nodes. For example, the top metal link vias ZTMs 163-1 can be used to connect other top metal layer adjacent to PMUT while they implement the vertical interconnections between the top metal layer 114 and the metal structure of stop layer 303 and the CMOS auxiliary circuits 300-CMOS.

In the PMUT ultrasonic transducer suitable for high-density system integration in this example, a CMOS metal interconnect layer is utilized as a first layer of metal wiring, which works with a second layer of metal wiring to form a design of double-layer wiring. Thus, not only the interconnections with the CMOS are implemented, but also double-layer metal wiring routing density is increased. Therefore, the interconnectivity of the PMUT array is greatly improved, a plurality of ultrasonic transducers can be connected in series or in parallel, and high flexibility is provided for the PMUT array design; in addition, the metal wiring length and the area occupation are greatly reduced, thereby the chip area is reduced remarkably.

The aluminum metal TSV pads 162-2 in the figures are aluminum structures that must be designed specially in the CMOS manufacturing process. They form a metal structure of stop layer for TSV etching, are helpful for stopping the TSV etching at specific positions, and form electrical connections from the TSVs to the other CMOS circuits. The structures may be arranged integrally with the metal interconnect layer for the CMOS units, or may be arranged separately and interconnected with the metal interconnect layer for the CMOS units.

The bonding metal mini-pads 300-1 and 300-2 in the figures are located at the side of the substrate material 160 and the side of the mechanical layer 130 respectively, and are arranged to meet the requirement of the wafer bonding process in the manufacturing method. The electrical connections between the wafers are implemented through the bonding metal mini-pads 300-1 and 300-2, then the PMUT array are vertically connected with the TSV welding balls from top to bottom through the metal wiring and the metal link vias.

In the PMUT ultrasonic transducer suitable for high-density system integration in this example, the metal electrodes in the sandwiched stack structure of the piezoelectric layer are vertically interconnected to the second layer of metal wiring through the metal link vias in vertical orientation, then vertically interconnected to the first layer of metal wiring (the metal interconnect layer for the CMOS units) through the metal lead vias in vertical orientation, and then interconnected to the back side of the silicon chip through the Through-Silicon Vias (TSVs). With the vertical wiring design described above, the majority of the bonding mini-pads and metal lead wires in the existing planar PMUT can be omitted, and the metal wiring is led vertically to the back side of the wafer, thereby a transition of the metal wiring from two-dimensional (2D) planar wiring to three-dimensional (3D) wiring, and the chip size and the package volume can be reduced remarkably.

In the SOC ultrasonic transducer suitable for high-density system integration in this example, the CMOS auxiliary circuits of the ultrasonic transducer array are integrated from conventional discrete circuits into the 3D architecture of the ultrasonic transducer through 3D vertical interconnections of the metal wiring, thereby a 3D architecture of System-On-Chip (SOC) is formed, the level of system integration is greatly improved from chip level to system level while the level of chip integration is improved, and system-level miniaturization is realized.

Example 2

In this example, a SOC ultrasonic transducer suitable for high-density system integration is provided. Similar to the architecture of the example 1, in consideration of the overall design of the SOC PMUTs, multi-layer wiring may be required for implementing interconnections in the case that the resolution requirement is high and a large-size array is required. For example, if an artificial intelligence algorithm is also included in the SOC PMUT ultrasonic transducer design, 5 to 6 layers of metal wiring may be required for the CMOS IC design. In the process flow of the present invention, the wiring architecture has been considered specially, and the process flow has high flexibility in terms of the number of wiring layers. Therefore, in this example, based on the example 1, at least one layer of metal wiring is further arranged above the second layer of metal wiring, and each layer of metal wiring in the at least one layer of metal wiring is vertically interconnected through metal lead vias, the bottommost layer of metal wiring in the at least one layer of metal wiring is vertically interconnected with the second layer of metal wiring through metal lead vias, and the topmost layer of metal wiring in the at least one layer of metal wiring is electrically interconnected with the bonding metal mini-pads 300-1 arranged on the hybrid bonding interface of the first wafer. Each layer in the at least one layer of metal wiring is further divided into two metal wirings, and the two metal wirings in the same layer are vertically interconnected with the two metal wirings in the next layer through two metal lead vias respectively.

In the case that a smaller size of CMOS circuit is required (e.g., 90 nm), the metal material may be changed from aluminum to copper. Such a change is encompassed by standard practices in the CMOS domain, and will not be further detailed here.

Example 3

In this example, a method for manufacturing the ultrasonic transducer suitable for high-density system integration by replacing the conventional planar wiring with vertical electrically interconnections is provided. In a SOC PMUT ultrasonic transducer, the PMUT top metal layer 114 is vertically connected to the metal structure of stop layer 303 and the second layer of metal 302 of the corresponding CMOS auxiliary circuits 300-CMOS respectively through the top metal link vias ZTMs 163-1; the bottom metal layer 112 is vertically connected to the metal structure of stop layer 303 and the second layer of metal 302 of the corresponding CMOS auxiliary circuits 300-CMOS through the bottom metal link vias ZBMs 163-2, and then vertically connected to any component in the CMOS auxiliary circuits 300-CMOS through the two metal lead vias 312. Through reasonable wiring, a plurality of ultrasonic transducers can be connected in series or in parallel.

The CMOS auxiliary circuits 300-CMOS can be connected to the CMOS unit 160-CMOS in the first wafer through the bonding metal mini-pads 300-1 and 300-2, then connected to the back side of the silicon chip through the Through-Silicon Vias (TSVs) 162, and then connected to the printed circuit board (PCB), so as to realize electrically interconnections.

In this example, through the vertical electrical interconnections, four layers, i.e., the PMUT array, the CMOS high-voltage auxiliary circuit chip, a second CMOS low noise amplifier controller chip, and the TSVs, are vertically stacked. Compared with the conventional planar process method, the chip size and the system volume are greatly reduced in this example.

Figure 5:
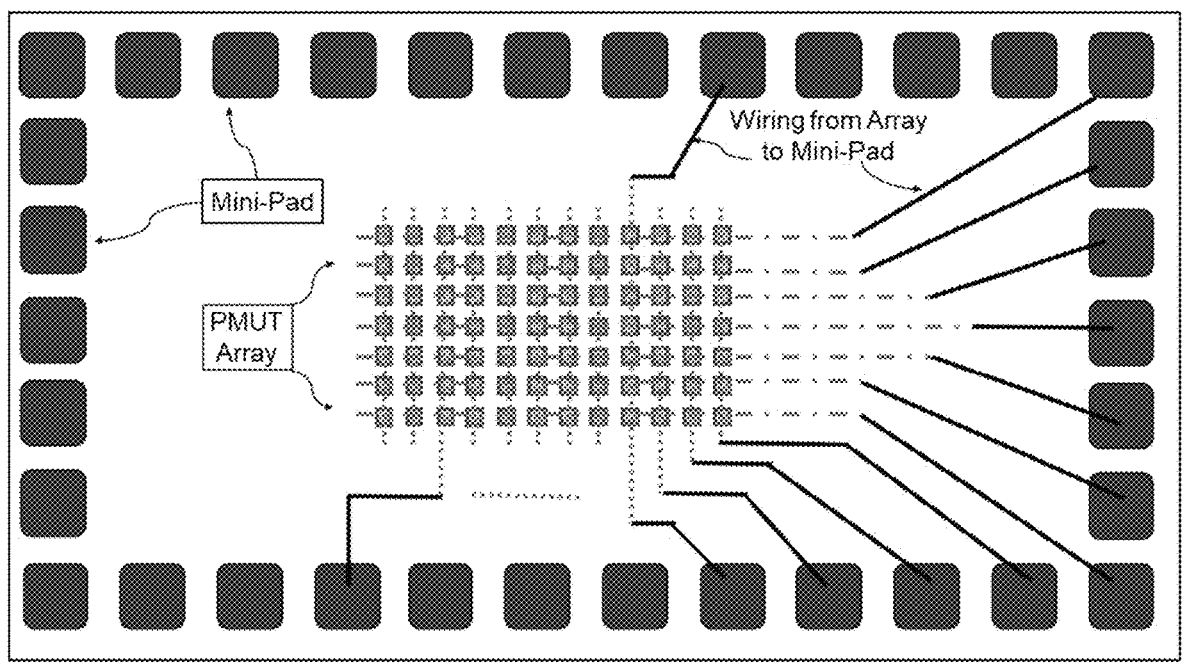
FIG. 5 is a schematic structural diagram of the existing PMUT array chip.
Figure 6:
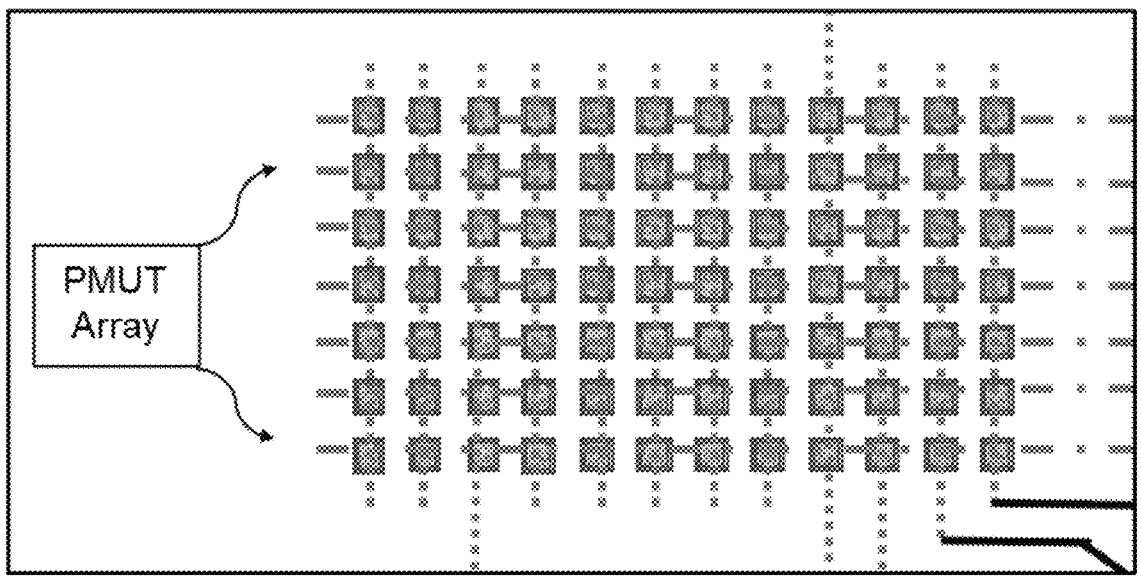
FIG. 6 is a schematic structural diagram of the PMUT array chip in the example 3 of the present invention.

As shown in FIG. 5, in an existing PMUT array chip product, a 2D PMUT array is arranged at the center of the chip, and bonding mini-pads are arranged on the periphery of the chip to implement electrical connections with the pins of the circuit package and connections with the bonding mini-pads of the CMOS auxiliary circuits. High-density lead wires are required to form electrical connections between the existing PMUT array chip and the peripheral circuits, and each metal wiring must meet the requirements for lead wire width and spacing under the design rules. Consequently, most of the chip area is used for the metal wiring rather than the active PMUT array itself and the chip area occupied by the metal wiring is much greater than the chip area occupied by the PMUT array. FIG. 6 shows the chip layout and wiring of a "7×12 array" formed by the ultrasonic transducers provided by the present invention. With the 3D ultrasonic transducers provided by the present invention, it is unnecessary to establish communication with the CMOS through bonding mini-pads arranged on the periphery of the array. Compared with the existing planar PMUT-on-CMOS interconnection architecture, the chip area occupied by the metal interconnections and the wiring length are greatly reduced.

Example 4

In this example, a manufacturing method of the PMUT ultrasonic transducer suitable for high-density system integration in the example 1 is provided. The process flow includes three parts.

The first part involves the process flow of CMOS circuits, for example, the process flow of PMUT pulse generation and control circuits. In this part, the standard process flow in the industry may be used, with the general compatibility with the 3D PMUT process and 3D Through-Silicon Via (TSV) process taken into account.

In the second part, first of all, the selected CMOS circuits are fabricated on a second wafer according to the division of the SOC block circuit diagram. The CMOS manufacturing process used for the second wafer may be completely different from that for the first wafer, depending on the SOC requirements. Next, the wafers are bonded and thinned. Then, the process flow of a PMUT 3D array is executed, including fabrication of PMUT units, metal interconnections, and special interconnections between the wafers, etc. The SOC PMUT structure proposed in this example is based on a hybrid bonding technique. The bonding interface for hybrid bonding mainly consists of silicon dioxide, with a metal structure (300-1) at the side of the wafer 1 and a metal structure (300-2) at the side of the wafer 2. The wafer bonding interface has a silicon oxide-silicon oxide interface and a metal-metal interface. When silicon dioxide is bonded together by fusion bonding while silicon oxide is bonded, the two wafers are electrically connected to each other via the metal structures 300-1 and 300-2 of the interface. The bonding interface is formed by oxides and metal in hybrid, hence the bonding is referred to as hybrid bonding.

The third part is the process flow of 3D Through-Silicon Vias (TSVs), and the focus of which is how to integrate the TSVs into the 3D architecture so as to form a part of the overall SOC process.

Actually, the three parts of the entire process flow are not completely separated from each other; instead, they are combined with each other and optimized as a whole. For example, the formation of a cavity is actually a part of the CMOS process. The aluminum landing pads required for the TSVs are also formed in the CMOS process. That is a result of overall design.

Figure 7:
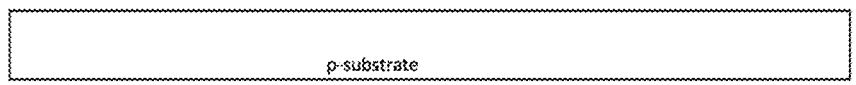
FIG. 7 is a first flow chart of the manufacturing process of a CMOS unit.
Figure 7:
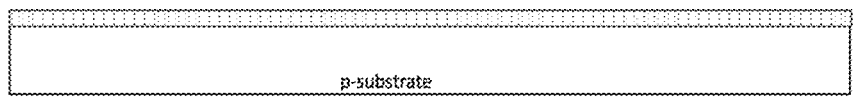
Figure 7:
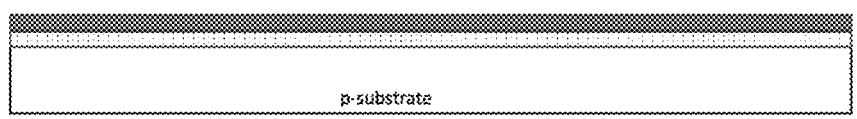
Figure 7:
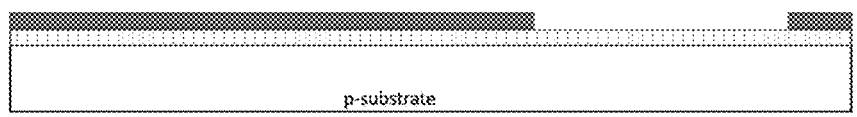
Figure 7:
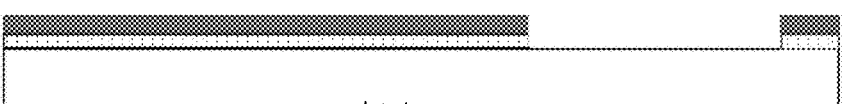
Figure 7:
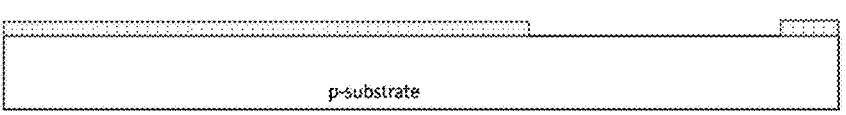
Figure 7:
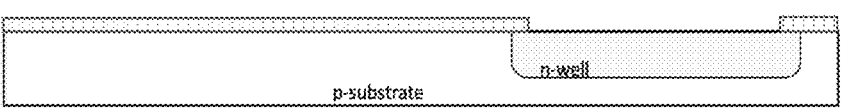
Figure 7:
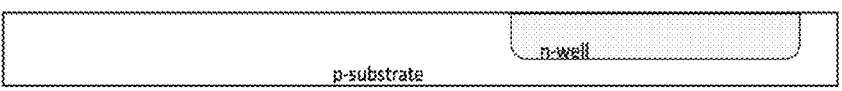
Figure 8:
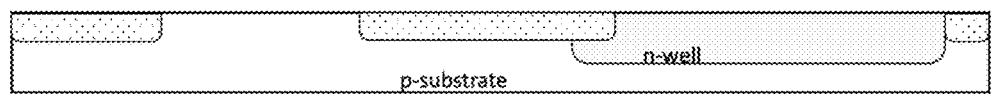
FIG. 8 is a second flow chart of the manufacturing process of a CMOS unit.
Figure 8:
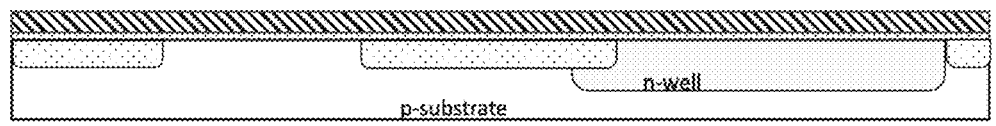
Figure 8:
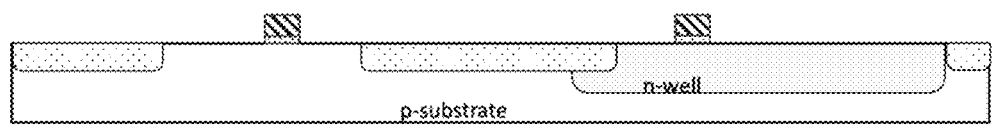
Figure 8:
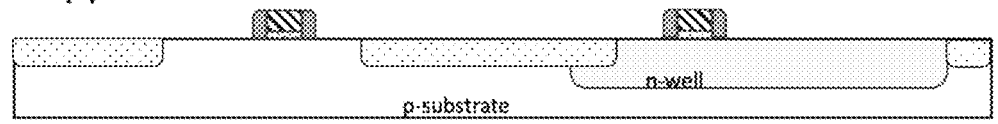
Figure 8:
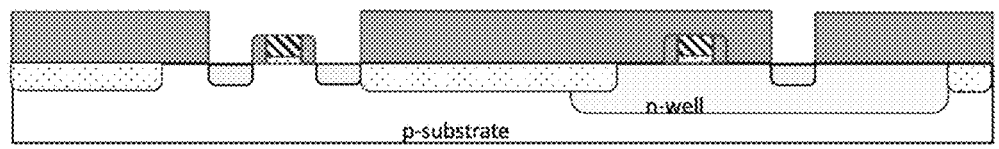
Figure 8:
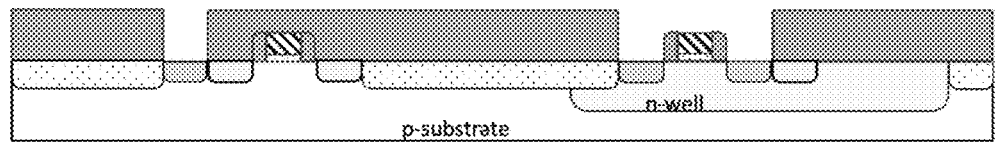
Figure 8:
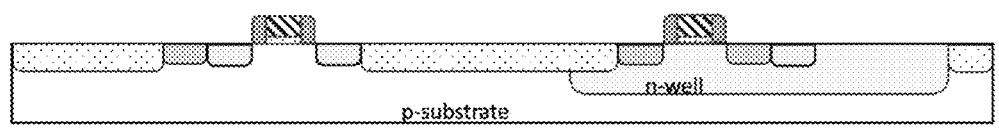
Figure 9:
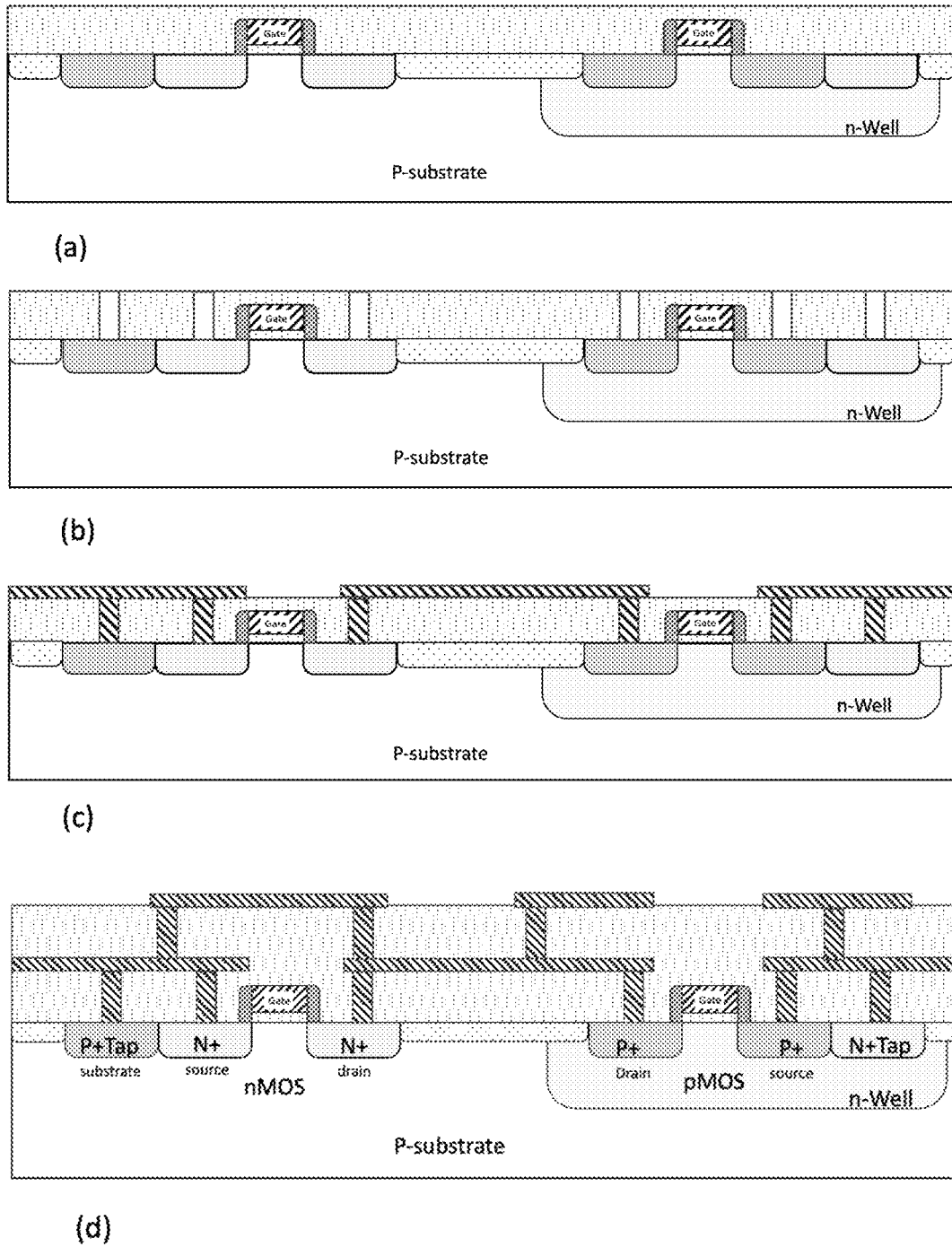
FIG. 9 is a third flow chart of the manufacturing process of a CMOS unit.

Specifically, the method comprises the following steps:

Step 1: preparing a first wafer, growing silicon dioxide in thickness of about 100 nanometers on the surface of the first wafer to form a silicon substrate, and manufacturing CMOS units on the silicon substrate. The CMOS circuit process is shown in FIGS. 7-9, and is implemented with the standard process in the industry. As shown in FIG. 7, the process includes the following steps: (a) preparing a starting material P-type silicon, (b) forming a silicon dioxide cushion layer, (c) coating a photoresist, (d) etching N-type wells, (e) etching an N-type well silicon dioxide layer, (f) and (g)

forming N-type wells by diffusion or ion implantation, and (h) removing the silicon dioxide cushion layer. Each layer of photo mask includes steps of coating a photoresist, exposure, photolithography and etching, and photoresist removing, which will not be described in details below. As shown in FIG. 8, the process further comprises the following steps: (a) forming an Active Region and a Shallow Trench Isolation (STI) region, while the traditional CMOS process may use local oxidation of Silicon (LCOS), (b) oxidizing transistor gate and depositing polysilicon, (c) photoetching polysilicon gate, etching, photolithography, LDD (Lightly Doped Drain) ion implantation, (d) forming spacer (transistor gate/source and drain self-aligned isolation) (e) photolithography of N+ source/drain region and N– connection region, ion implantation into the source/drain region, (f) photolithography of P+ source/drain region and P-substrate connection region, ion implantation into the source/drain region, and (g) removing the photoresist, rapid annealing to activate ion implantation, to complete the structure of MOS device. As shown in FIG. 9, the process further comprises the following steps: (a) depositing ILD (Inter-Layer Dielectric) dielectric layer, planarization refluxing or CMP, (b) photoetching contact vias, metal of contact vias (such as Ti/TiN/W) sputtering, W-CVD, W-CMP, (c) depositing the first layer of metal (Ti/TiN/AlCu/TiN), photolithography and etching. For the more advanced CMOS process, Cu metal interconnection will be used; the formation of contact vias, and the material and structure of metal interconnection will be different, which will not be discussed here.

In the overall SOC design, multi-layer wiring may be required for implementing the interconnections in the case that the resolution requirement is high and a large-size array is required. For example, if an artificial intelligence algorithm is also included in the PMUT-on-CMOS ultrasonic transducer design, 5 to 6 layers of metal wiring may be required for the CMOS IC design. In the process flow of the present invention, the wiring architecture has been considered specially, and the process flow has high flexibility in terms of the number of wiring layers. FIG. 9(d) illustrates two layers of metal wiring, and the same procedure can be applied to 5-6 layers of metal wiring.

Figure 10:
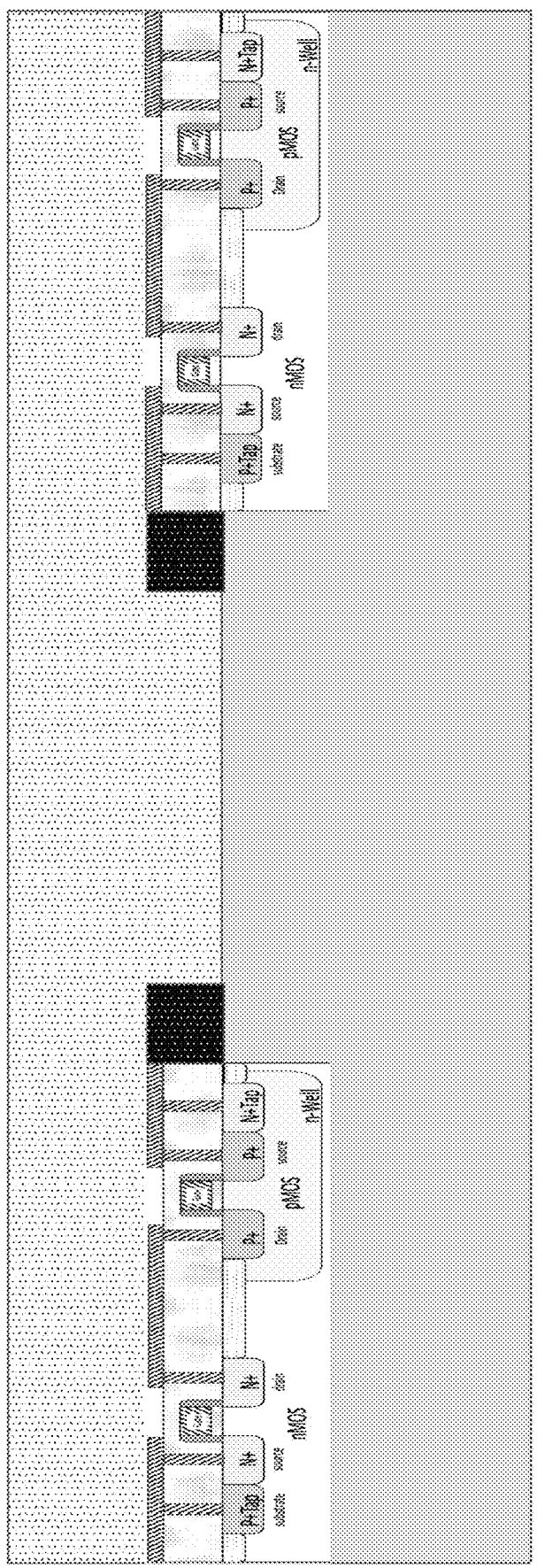
FIG. 10 is a schematic diagram of the process corresponding to the step 2-1 in the example 4 of the present invention.

Step 2: further manufacturing PMUT units on the CMOS units and integrating CMOS auxiliary circuits, specifically comprising:

Step 2-1: as shown in FIG. 10, first of all, it should be pointed out that the metal structures of stop layer 303 that must be considered specially in the design, the metal structures of stop layer 303 are the metal structures of stop layer etched through a dry process (i.e., a DRIE etch-stop layer) of the structures 163-1 and 163-2 in the hybrid bonding process. However, in the process, the metal structure 303 is a part of the first layer of metal wiring of the CMOS in nature. An Inter-Metal dielectric (IMD) layer of the CMOS circuit is deposited with silicon dioxide ($SiO_2$) in thickness of about 800 nanometers, then is performed with a chemical mechanical polishing (CMP) process to form a smooth and flat $SiO_2$ surface to facilitate the follow-up processes such as photoresist coating, etc.

Figure 11:
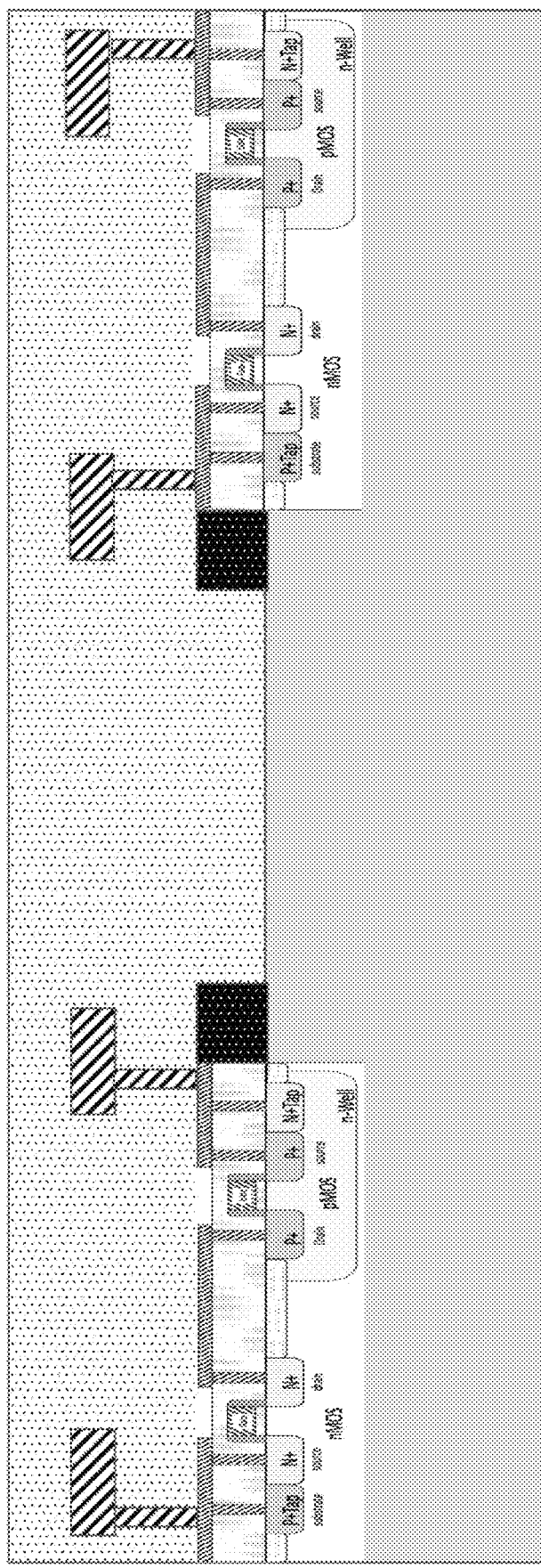
FIG. 11 is a schematic diagram of the process corresponding to the step 2-2 in the example 4 of the present invention.

Step 2-2: as shown in FIG. 11, forming metal lead vias between the metal wiring layers by photolithography and then etching through a dry plasma process to form vias, then removing the photoresist, and cleaning; then, performing titanium/titanium nitride sputtering and aluminum deposition on the hot substrate to fill the interconnection vias (if the vias are very small, the aluminum deposition may be replaced by chemical vapor deposition of tungsten to form the vias); next, depositing a metal layer, and performing photolithography and etching to form a second layer of metal wiring, removing the photoresist and cleaning.

Depositing a $SiO_2$ substrate material at a low temperature, and chemically and mechanically polishing the substrate material to form a flat surface of the substrate material.

The $SiO_2$ deposition (plasma enhanced chemical vapor deposition, PECVD) at a low-temperature is performed at 250 to 300° C., and the thickness of the $SiO_2$ is about 3 sm. Then, chemical and mechanical polishing is carried out to form a smooth and flat $SiO_2$ surface. In connection with the special process steps of PMUT-on-CMOS, a silicon dioxide-silicon nitride-silicon dioxide sandwich structure is introduced in the dielectric layer (similar to the passivation layer in the CMOS process), at the part where a cavity 120 is to be formed, a layer of silicon nitride is deposited under the silicon dioxide at the bottom of the cavity; in view that the silicon dioxide etching rate is much higher than the silicon nitride etching rate, a silicon dioxide dry etching process can be employed easily, and the etching stops at the silicon nitride layer; by forming the cavity in that way, the depth of the cavity can be controlled accurately, and the component can be miniaturized easily.

Figure 12:
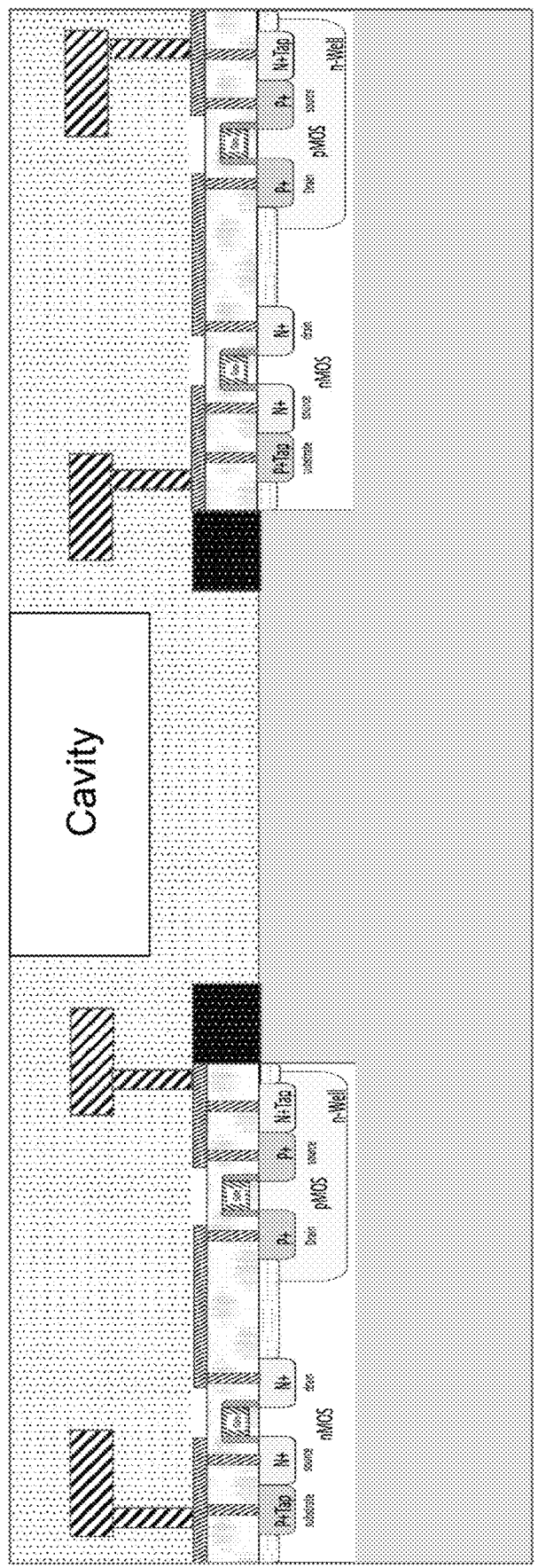
FIG. 12 is a schematic diagram of the process corresponding to the step 2-3 in the example 4 of the present invention.
Figure 13:
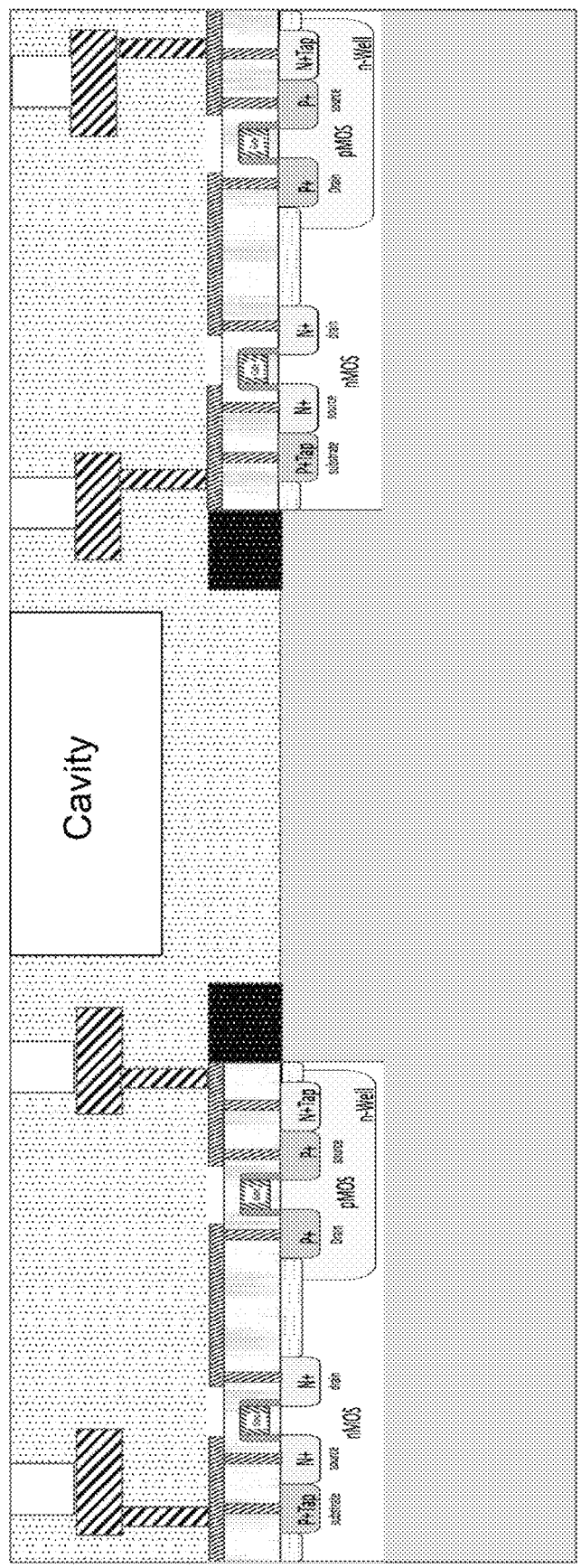
FIG. 13 is a schematic diagram of the process corresponding to the step 2-4 in the example 4 of the present invention.

Step 2-3: as shown in FIG. 12, performing photolithography and etching to form a silicon dioxide cavity: coating a photoresist, performing photolithography to form a cavity pattern, and etching the $SiO_2$ with plasma chemical vapor to form a cavity in depth of about 2 μm; then removing the photoresist and cleaning;

Step 2-4: as shown in FIG. 13, performing photolithography and etching to form bonding metal mini-pads 300-2 required for hybrid bonding: coating a photoresist, performing photolithography to form patterns, and etching the $SiO_2$ with plasma chemical vapor, till the second layer of aluminum is reached; then removing the photoresist and cleaning. The vias in the bonding metal mini-pads 300-2 are shallow, in depth of 0.2 to 0.3 μm.

Figure 14:
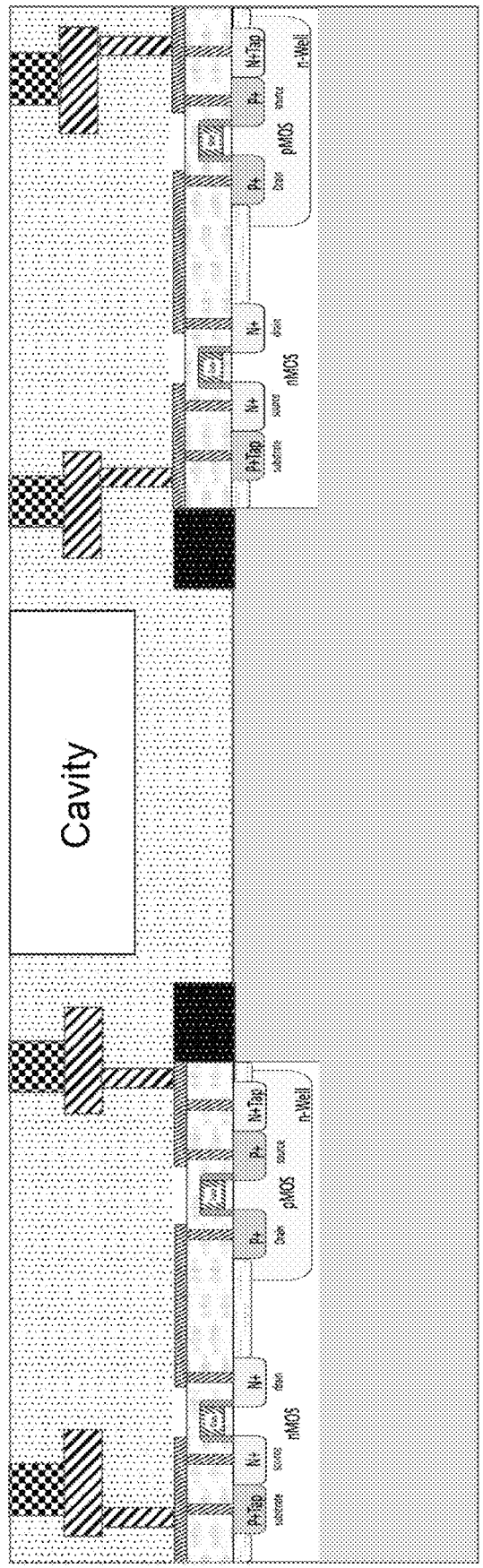
FIG. 14 is a schematic diagram of the process corresponding to the step 2-5 in the example 4 of the present invention.

Step 2-5: as shown in FIG. 14, forming metal mini-pads 300-2 by metal deposition and CMP; forming mini-pads 300-1 on the other wafer in the same way. The positions of the mini-pads on the two wafers are designed accurately, so that the bonding metal mini-pads 300-1 and 300-2 can be butt jointed and interconnected during wafer bonding.

Figure 15:
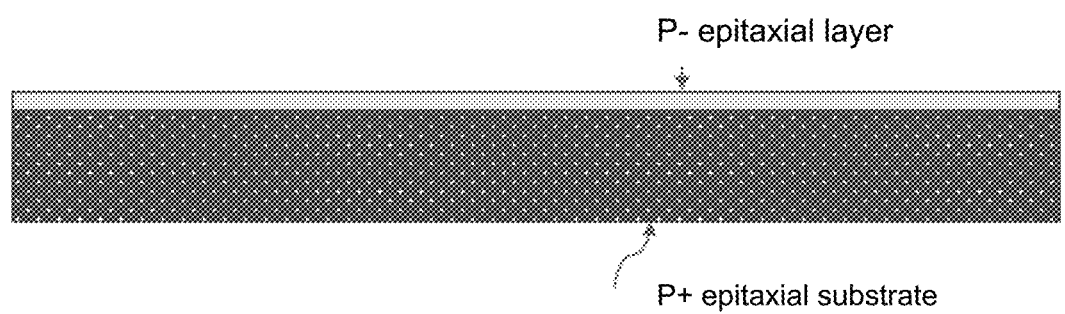
FIG. 15 is a schematic diagram of the second wafer in the step 2-6 in the example 4 of the present invention.
Figure 16:
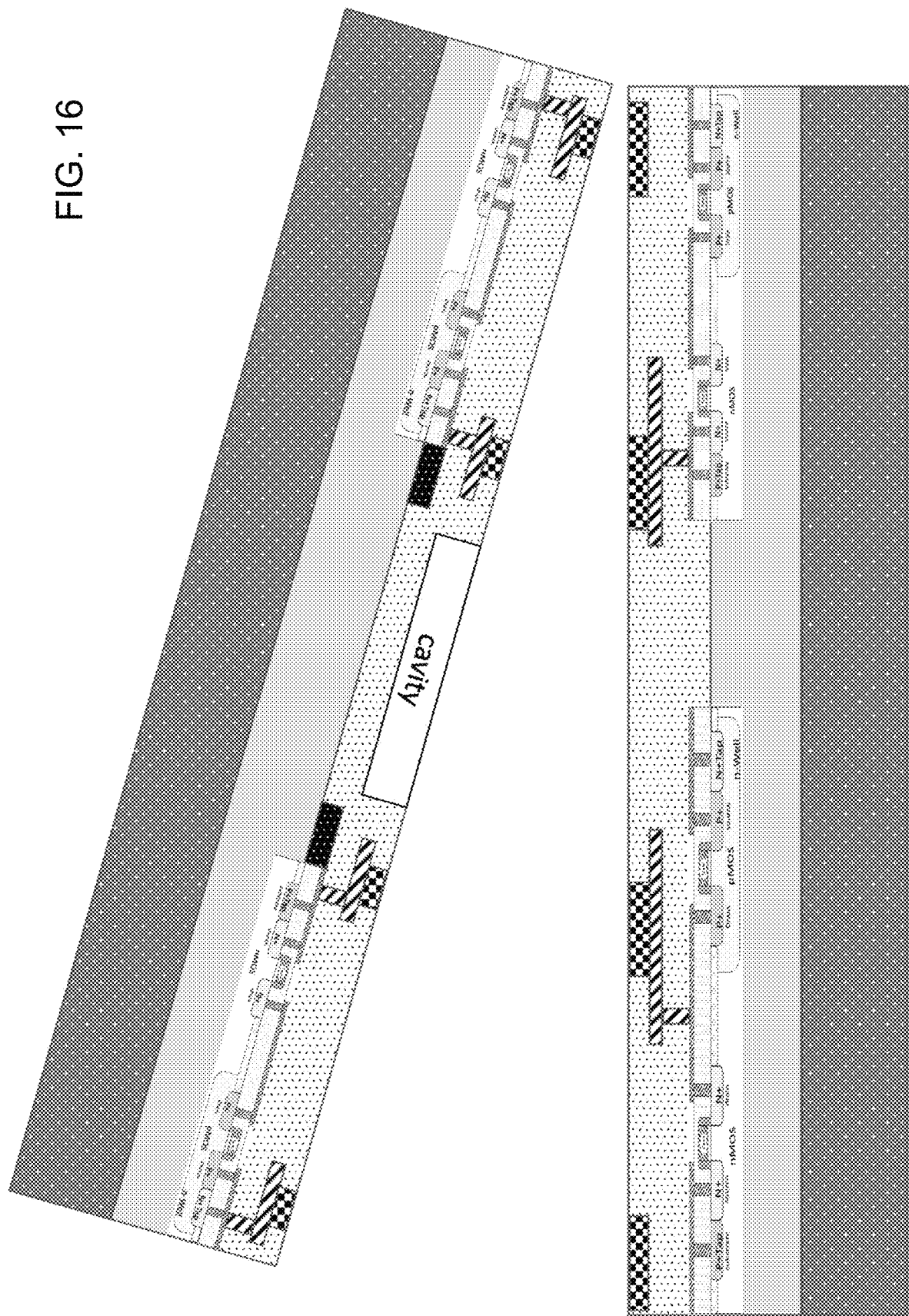
FIG. 16 is a schematic diagram of the CMOS circuit manufactured in the step 2-6 in the example 4 of the present invention.
Figure 17:
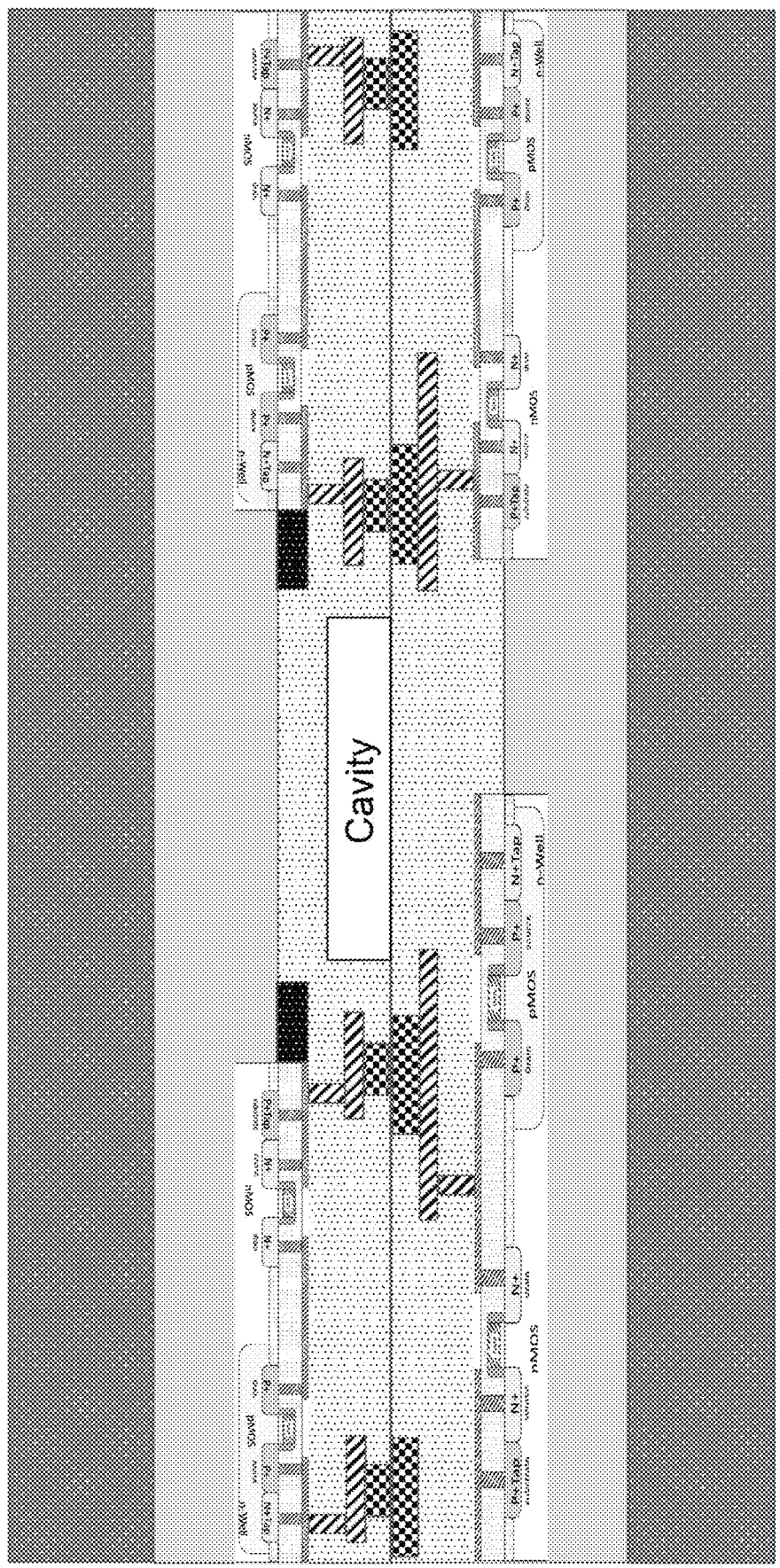
FIG. 17 is a schematic diagram of the bonding in the step 2-6 in the example 4 of the present invention.

Step 2-6: as shown in FIGS. 15-17, preparing a second wafer, growing silicon dioxide in thickness of about 100 nanometers on the surface of the second wafer to form a silicon substrate, fabricating required CMOS circuits on the silicon substrate, and bonding the second wafer to the first wafer. The CMOS circuit manufacturing process is the same as that in the step 1, and is implemented with the standard process in the industry.

There are some special considerations in preparation of the second wafer. The starting material of the wafer is a P–/P+ epitaxial wafer. The thickness of the epitaxial layer is related with the required final thickness of the PMUT mechanical layer. The concentration difference of the P–/P+ layer should be higher than one order of magnitude, so that the thickness of the remaining wafer can be well controlled during chemical thinning.

After the CMOS process is completed, whether to adjust the thickness of the $SiO_2$ is determined according to the design requirement for the depth of the cavity (determined by the maximum displacement of the piezoelectric material in the vertical direction), then photolithography and etching are performed to the $SiO_2$ cavity to achieve different depth of cavity.

A particular advantage of this example is that a cavity can be formed on each of the two wafers respectively before the bonding, and there are two cavities after the bonding. The two aligned cavities are combined into one cavity, the combined cavity has greater depth and can output ultrasonic waves at higher power. For general applications, a single cavity design is enough, and it is unnecessary to design multiple cavities. From the point of view of the SOC design, it is better to arrange the cavity at the side of the mechanical layer. For simplicity, only one cavity is described in the following process flow, and the cavity is arranged in the mechanical layer.

Lately, a hybrid interface bonding technique has been developed in the semiconductor industry. With that technique, a small amount of metal (bonding metal mini-pads 300-1 and 300-2), for example, copper, exists on the bonding interface. When a first wafer is bonded with a second wafer, the metal mini-pads 300-1 and 300-2 are aligned and contact with each other, and electrical connections are formed between the copper, while most of the silicon dioxide is bonded.

In this example, the hybrid bonding technique is applied to PMUT applications for the first time, and a SOC scheme is employed to bring its technical potential into full play. After the plasma treatment of the $SiO_2$ surfaces, the $SiO_2$ surfaces of the wafers are aligned face to face, pressurized, heated, and annealed, so that the bonding of the metal mini-pads 300-1 and 300-2 is realized and hybrid bonding is completed while the fusion bonding between silicon dioxide is completed.

An advantage of the hybrid bonding technique is that the two wafers are electrically interconnected while they are bonded, without the etching of Z-shaped metal connection vias in large depth. The process is relatively simple and convenient. However, hybrid bonding has a higher requirement for the flatness of the bonding interface, and the electrical connections may be unreliable even if there is any tiny step smaller than one nanometer between the oxide and the copper during the bonding.

Figure 18:
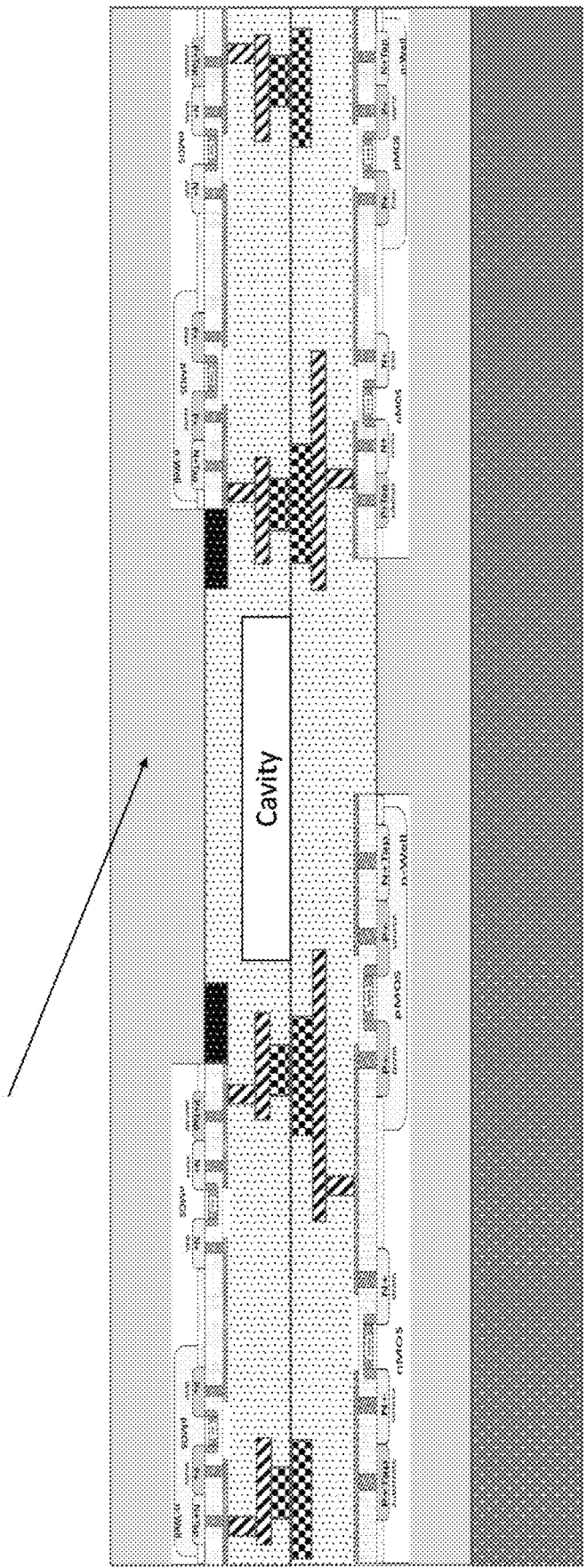
FIG. 18 is a schematic diagram of the thinning process in the step 2-7 in the example 4 of the present invention.

Step 2-7: as shown in FIG. 18, grounding the back side of the second wafer to reduce the thickness to less than 100 μm after the bonding is completed; then, carrying out etching with a chemical liquid to further reduce the thickness of the wafer to 5 to 8 μm, and finally carrying out chemical mechanical polishing (CMP) till the remaining thickness of the wafer is 2 to 5 μm.

The materials commonly used for the structure of the mechanical layer 130 in the industry include silicon oxide, silicon nitride, polysilicon, or a multi-layer film composed of these materials in combination. All of these materials are not monocrystal materials. In other words, owing to the disordered morphology of the molecular structures of these materials, the mechanical properties and parameters of these materials and the mechanical stress in the film are affected by the conditions of the manufacturing process, and the controllability and repeatability of the manufacturing process are poor. More seriously, the PMUT film is not flat, but somewhat adhesive in its initial state owing to the disordered morphology, the internal residual stress, and the effect of the surface charges. In the wafer bonding and thinning method proposed in this example, a silicon monocrystal is introduced into the mechanical layer. Since the silicon is a high-quality and high-strength monocrystal, the repeatability of the mechanical parameters of the mechanical layer is optimal, the internal mechanical stress is minimized. Therefore, the uniformity and the manufacturing repeatability are better. Moreover, the conductive silicon material can effectively release electric charges and reduce adhesion.

Figure 19:
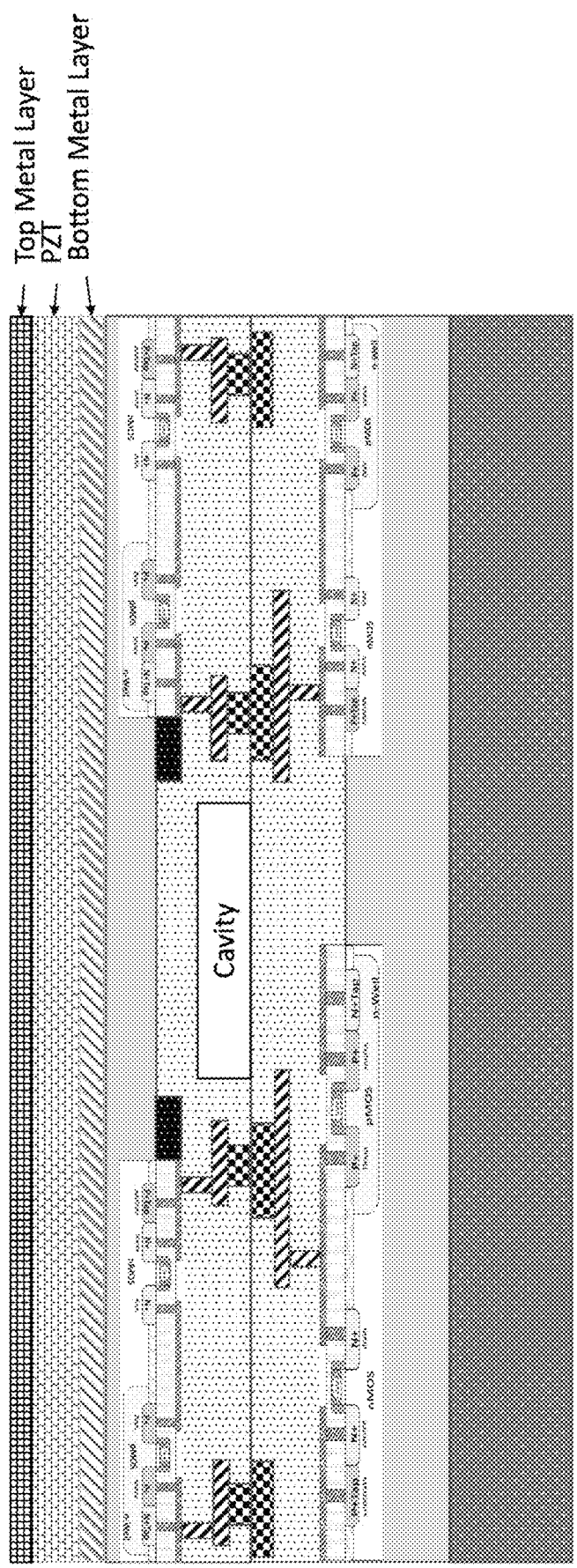
FIG. 19 is a schematic diagram of the process corresponding to the step 2-8 to step 2-10 in the example 4 of the present invention.

Step 2-8: as shown in FIG. 19, performing metal deposition to form a bottom metal layer: a multi-layer structure formed by a titanium (Ti) layer in thickness of 20 nm and a platinum (Pt) layer in thickness of 100 nm is employed. The titanium (Ti) increases the adhesion between the metal layer and silicon and silicon oxide, and the platinum (Pt) is one of the best conductive materials and can improve piezoelectric efficiency. The Ti layer is formed by sputtering, and the Pt layer is formed by evaporation in vacuum with an electron gun at heavy current and high temperature.

Step 2-9: as shown in FIG. 19, depositing a piezoelectric material to form a piezoelectric material layer.

The piezoelectric material may be PZT or other piezoelectric materials, such as AlN. Here, we take PZT as a representative to describe. PZT deposition is completed by sputtering. The PZT (lead zirconate titanate, $Pb(ZrTi)O_3$, PZT for short) is a solid target material prepared by mixing at a special atomic ratio in advance. In high vacuum, the PZT target material is sputtered and deposited on the surface of the wafer by plasma generated under high voltage. While sputtering, a certain temperature is applied to the silicon substrate for the PZT to recrystallize to form a desired piezocrystal. The deposited thickness of the PZT is about 1 μm. The AlN material is also formed by sputtering, and the operating temperature during the sputtering may be lower (lower than 400° C. or even lower), which is more beneficial to reduce the influence of temperature on the existing metal in the subsequent process integration.

In this example, the process details are described in connection with PZT. Through an appropriate adjustment in terms of the components and the process architecture, this example is fully applicable to aluminum nitride PMUT The architecture of this example is also applicable to the SOC design of CMUT and can achieve performance improvement similar to that in the case of PMUT.

Figure 20:
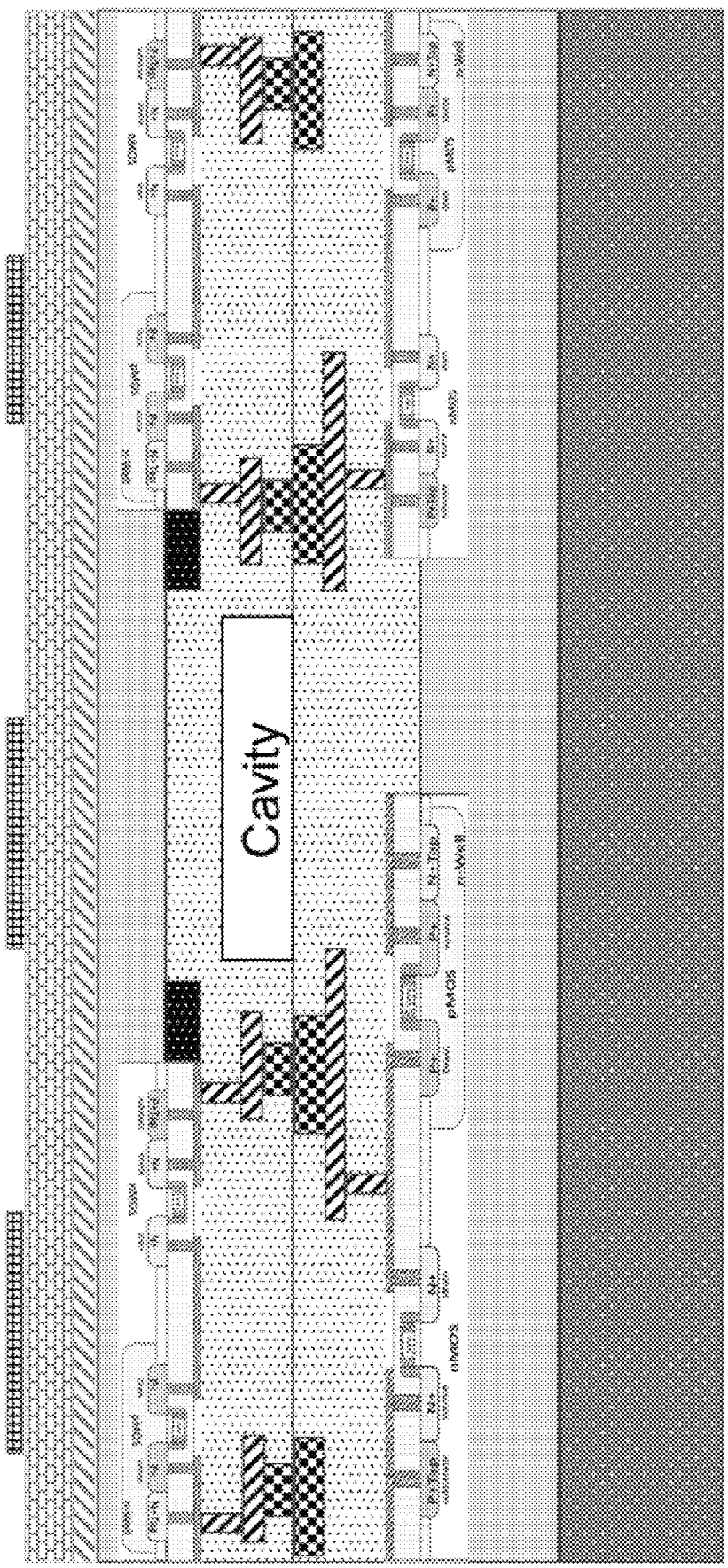
FIG. 20 is a schematic diagram of the process for forming the top metal layer in the step 2-10 in the example 4 of the present invention.

Step 2-10: as shown in FIG. 20, depositing the top metal and performing photolithography and etching to the top metal to form a top metal layer. Platinum (Pt) is also used in the PZT top metal layer deposition, and the thickness of Pt is 100 nm (0.1 μm). In view that platinum (Pt) is an inert metal and it is difficult to shape Pt by liquid etching, the top metal layer is etched by plasma dry vapor etching in this example.

Figure 21:
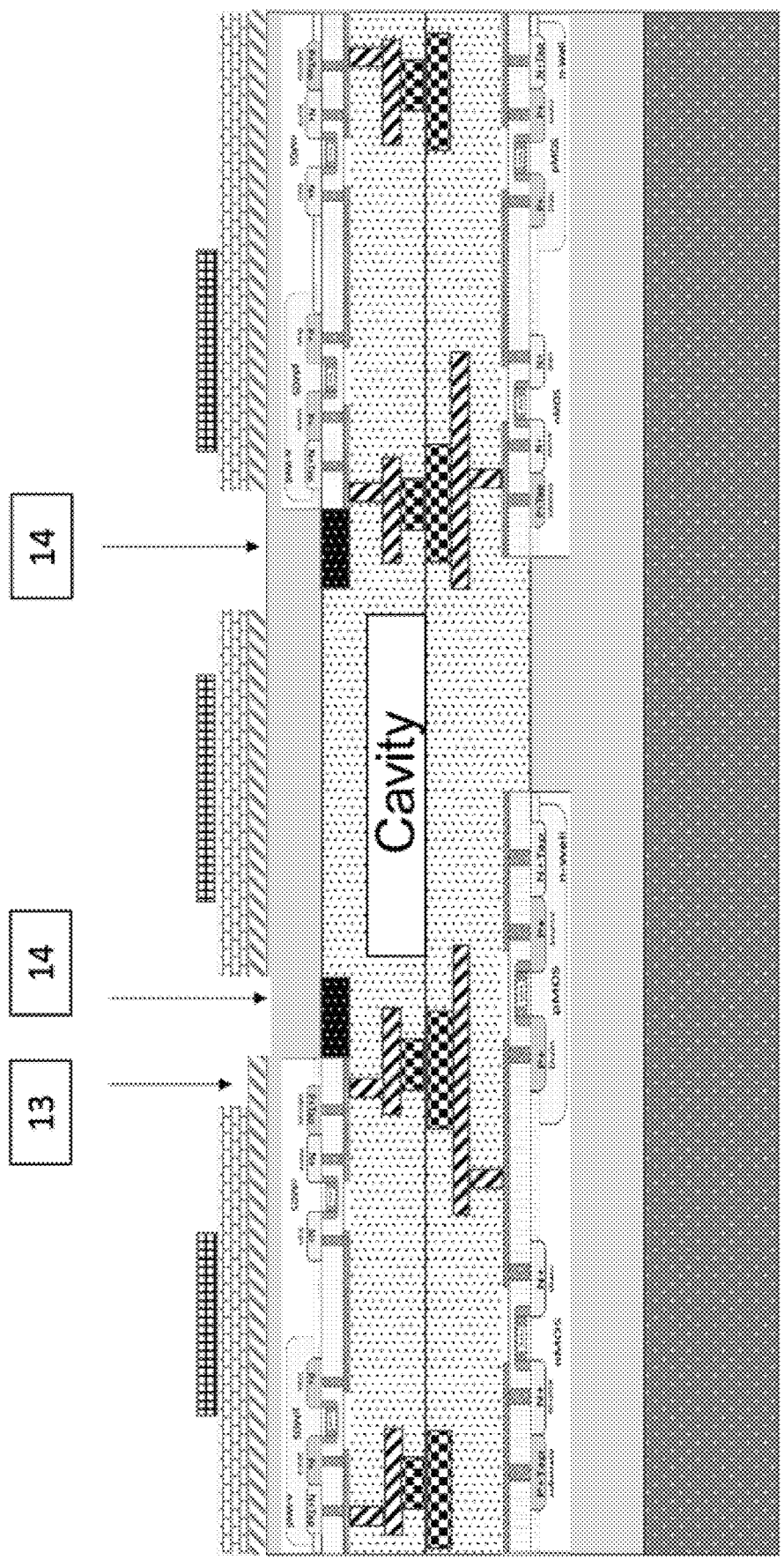
FIG. 21 is a schematic diagram of the PZT and bottom metal layer etching process in the step 2-11 in the example 4 of the present invention.
Figure 22:
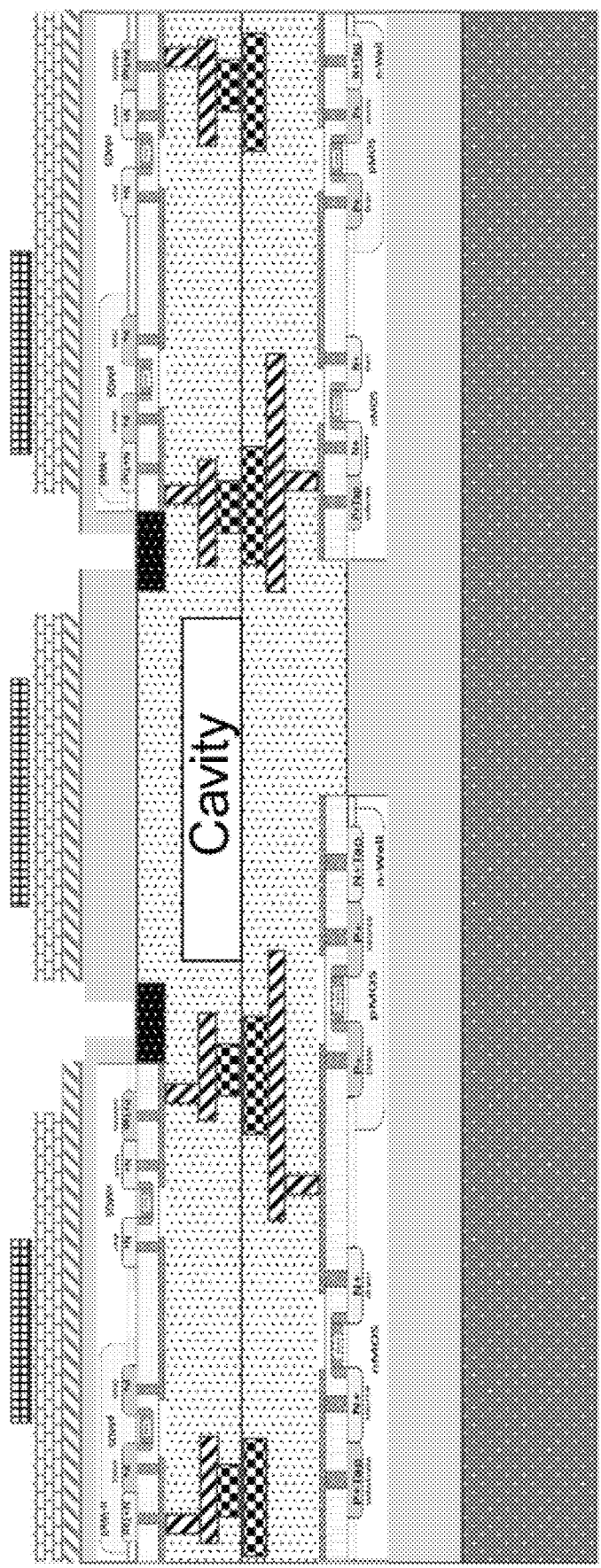
FIG. 22 is a schematic diagram of the vertical via etching process in the step 2-11 in the example 4 of the present invention.
Figure 23:
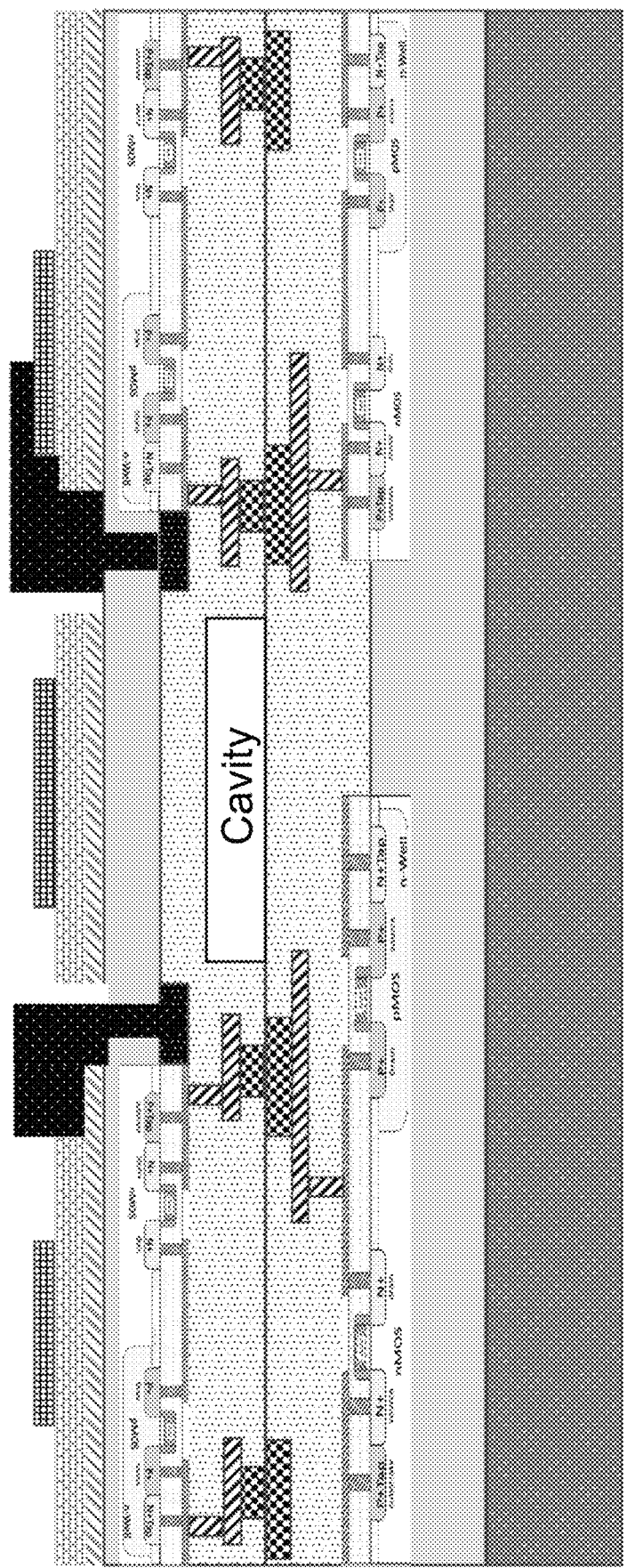
FIG. 23 is a schematic diagram of the Ti/TiN/Al deposition process in the step 2-11 in the example 4 of the present invention.

Step 2-11: as shown in FIGS. 21-23, performing photolithography and etching, and metal deposition and filling to form metal link vias.

In view that the metal link vias are Z-shaped vias, PZT etching is carried out first to etch the PZT only, as shown in the region 13 in FIG. 21. The PZT etching is carried out through a world-leading plasma dry vapor etching process with hydrogen chloride hydrogen fluoride, which not only achieves high etching uniformity but also forms neat PZT edges after etching, with certain slope, to facilitate the follow-up procedures. The AlN material may be etched with phosphoric acid or through a corresponding plasma dry etching process after appropriate adjustment of the process. Then, the PZT and the underlying metal are etched, as shown in the region 14 in FIG. 21. In this step, the PZT and the underlying metal are etched at the same time through a plasma dry vapor etching process. As shown in FIG. 22, then Z-shaped vertical vias (Zias) are formed by photolithography and etching. A key structure for the 3D electrical connections in the vertical direction is the Z-shaped vertical vias (Zias), which connect the top metal layer and the bottom metal layer of the PMUT to the metal structure of stop layer 303 in the vertical direction and then to other parts of the circuits through the first layer of metal wiring 301, the metal lead vias 321, and the second layer of metal wiring 302 of the CMOS auxiliary circuits. After the photoetching vias Zias are formed, the mechanical layer and the silicon dioxide layer are etched, and the etching is stopped at the metal structure of stop layer 303, then the photoresist is removed, and the structure is cleaned. As shown in FIG. 23, after the surfaces are insulated and the bottoms of the connecting vias are cleaned by sputtering, then Ti/TiN/Al deposition is carried out, wherein Ti/TiN is formed by sputtering, and aluminum is deposited by using a hot substrate deposition method, to improve the effect of aluminum filling into the Zias. Finally, metal photolithography and etching are carried out to form required wiring. If the size of the Zias is small (<1 μm), the aluminum may be replaced by CVD tungsten, so that the Zias can be filled better.

Step 2-12: performing metal photolithography and etching to form required wiring.

Figure 24:
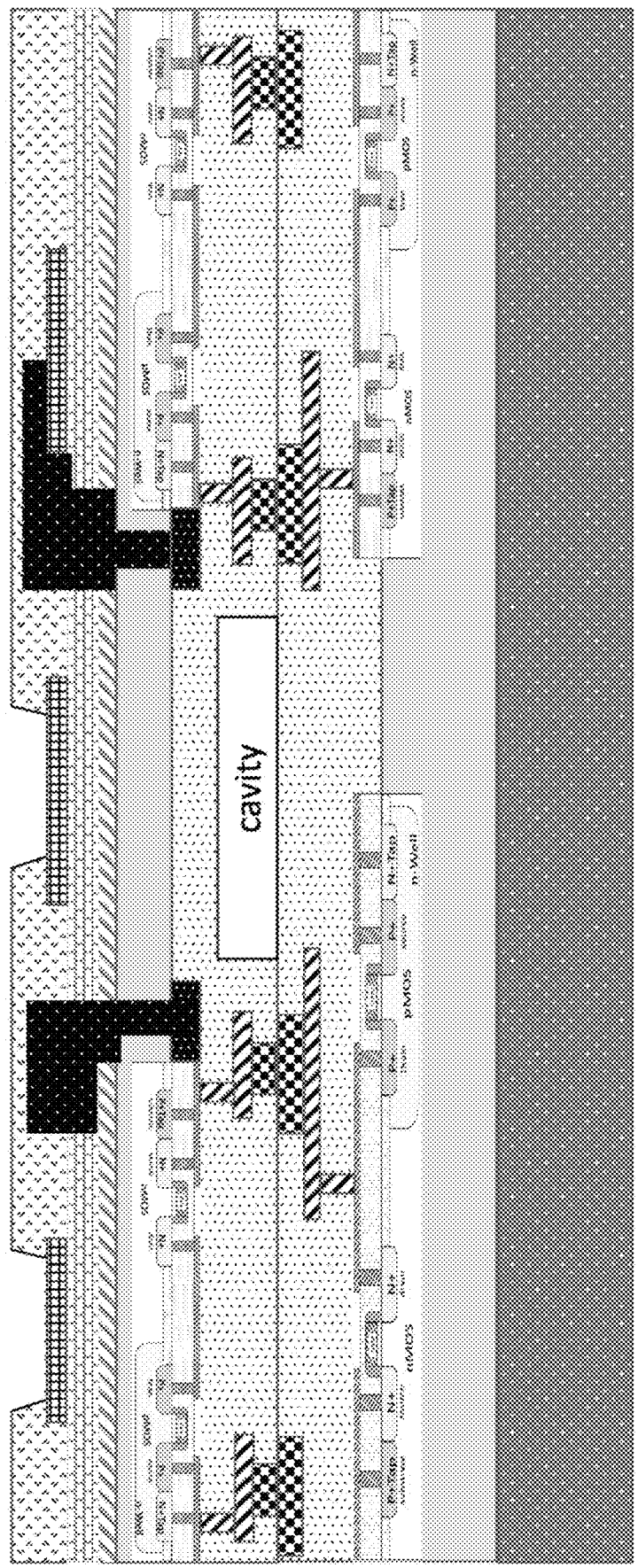
FIG. 24 is a schematic diagram showing that a passivated protection layer is added after completing the step 2 in the example 4 of the present invention.

Step 3: as shown in FIG. 24, performing photolithography and etching through the front and back side of the silicon substrate and performing metal deposition to form Through-Silicon Vias (TSVs). Specifically, this step comprises the following sub-steps:
(a) protecting the front side of the PMUT wafers: forming a cavity, and covering the cavity with a passivated protection layer;
(b) thinning the silicon substrate by grinding;
(c) forming mini-pads and performing selective etching and thinning to scribe lines;
(d) forming a metal layer on the back side;
(e) performing laser boring to the mini-pads;
(f) performing sputtering (Ti/Cu) and plating copper;
(g) etching wiring on the back side;
(h) plating nickel and gold (Ni/Au) and etching ball bonding regions;
(i) forming ball bonding array on the back side.

In this example, aluminum TSV pads 162-2 are used for the metal structure of stop layer (etch stop landing pads) for TSV etching, and a TSV pad array is used to directly weld the SOC PMUT array to the printed circuit board (PCB). Thus, the structure size is small, fewer external lead wires are used, and the method is very helpful for system miniaturization.

Thus, in this example, two active wafers with preformed CMOS circuits are bonded, metal link vias are formed for connections in the vertical direction, multi-layer metal wiring is used to improve the wiring efficiency, and the metal interconnections are led through TSVs from the front side of the wafer to the back side of the wafer. In that way, all manufacturing procedures for the PMUT SOC units suitable for high-density system integration are completed, the chip area occupied by the metal wiring is minimized, and the chip size and the system volume are reduced.

The manufacturing process flow of the PMUT SOC units in this example is compatible with the mainstream semiconductor processes and equipment, and the vertical wiring connections are compatible with the existing BGA (Ball Grid Array) chip packaging process. Therefore, the method provided by the present invention has wide adaptability.

The following aspects must be considered to effectively integrate the CMOS auxiliary circuits required for the operation of an ultrasonic transducer into a 3D SOC architecture:

Since a PMUT requires high-voltage pulsed control signals to generate ultrasonic signals, from the perspective of system integration, it is reasonable to integrate the high-voltage pulsed control signal circuit and the PMUT chip/array on the same wafer to realize the shortest distance interaction. Similarly, the part of auxiliary high-voltage pulse circuits, such as high voltage source circuit and pulse modulation circuit, etc., should also be arranged on the same wafer.

When the PMUT receives ultrasonic waves and converts them into electrical signals, the electrical signals should be amplified by an analog small signal amplifier to increase the signal amplitude and reduce the noise. Then the signals should be processed by a variable gain control circuit to further improve the signal to noise ratio (SNR). In other words, the CMOS circuits required for ultrasonic reception and amplification is completely different from the high-voltage pulse circuit required for ultrasonic emission. From the point of view of SOC system classification, it is more reasonable to arrange the circuits related to ultrasonic reception and signal amplification on the same wafer.

During SOC system classification, one of the key considerations is the overall complementarity of the CMOS process and overall cost. First of all, circuits using similar process flow and similar design rules should be arranged on the same wafer as much as possible. For example, the high-voltage pulse circuit, the source circuit for generating high-voltage, and the high-voltage regulating circuit, etc., usually use CMOS processes with large design rules. Generally, the transistors used in high-voltage circuits have larger geometric dimensions to ensure a breakdown voltage that is high enough. On the other hand, high SNR analog amplifiers can be easily realized by using advanced processes with smalls design rules, and high-resolution analog-to-digital converters also require advanced processes. Therefore, it is more reasonable to arrange the designs that require advanced processes on the same wafer.

In addition, the costs of making high-voltage devices in the advanced manufacturing processes are relatively high. If high-voltage and normal-voltage circuits are involved in the same CMOS manufacturing process, the manufacturing process will be complicated, and more photo mask layers are required. Ultimately, the chip cost will be high, and the product yield will be lowered owing to the complicated process.

During SOC system classification, the factors to be considered are closely related with the content of system integration.

The present invention is the most beneficial to intelligent ultrasonic scanners, especially portable scanners with artificial intelligence functions.

The invention claimed is:

1. An SOC PMUT suitable for high-density system integration, comprising: a first wafer and a second wafer, wherein a silicon substrate (160) is arranged on the first wafer, at least one CMOS unit is arranged above the silicon substrate (160), and a metal interconnect layer (201) of the at least one CMOS unit is vertically interconnected with a second layer of metal wiring (202) above the metal interconnect layer (201) through metal lead vias (212); Through-Silicon Vias (TSVs) (162) are arranged in the silicon substrate (160) for vertically interconnecting the metal interconnect layer (201) with the back side of the silicon substrate (160); the first wafer and the second wafer are stacked by hybrid bonding, and the first wafer and the second wafer are electrically interconnected by bonding metal mini-pads (300-1, 300-2) arranged on hybrid bonding interfaces of the two wafers; the bonding metal mini-pads (300-1) arranged on the hybrid bonding interface of the first wafer are electrically interconnected with the second layer of metal wiring (202); a mechanical layer (130) of the SOC PMUT is arranged on the second wafer, at least one cavity (120) is arranged under the mechanical layer (130), at least one CMOS auxiliary circuit for supporting the operation of the SOC PMUT is arranged in the mechanical layer (130), and a metal interconnect layer (301) of the CMOS auxiliary circuit is vertically interconnected with a second layer of metal (302) under the metal interconnect layer (301) through metal interconnection vias (312); the second layer of metal (302) is electrically interconnected with the bonding metal mini-pads (300-2) arranged on the hybrid bonding interface of the second wafer; a bottom metal layer (112), a piezoelectric material layer (115) and a top metal layer (114) of the SOC PMUT are arranged above the mechanical layer (130), the metal interconnect layer (301) of the CMOS auxiliary circuit is vertically interconnected with the top metal layer (114) through top metal link vias ZTMs (163-1), and is vertically interconnected with the bottom metal layer (112) through bottom metal link vias ZBMs (163-2).

2. The SOC PMUT suitable for high-density system integration according to claim 1, wherein the mechanical layer (130) employs the same material as the silicon substrate (160).

3. The SOC PMUT suitable for high-density system integration according to claim 1, wherein a metal structure of stop layer (303) is arranged in the bottom layer of the mechanical layer (130), and the top metal link via ZTM (163-1) and the bottom metal link via ZBM (163-2) are electrically interconnected with the metal interconnect layer (301) of the CMOS auxiliary circuit through the metal structure of stop layer (303).

4. The SOC PMUT suitable for high-density system integration according to claim 1, wherein at least one layer of metal wiring is further arranged above the second layer of metal wiring (202) in the substrate material (160), and each layer of metal wiring in the at least one layer of metal wiring is vertically interconnected through metal lead vias, the bottommost layer of metal wiring in the at least one layer of metal wiring is vertically interconnected with the second layer of metal wiring through metal lead vias, and the topmost layer of metal wiring in the at least one layer of metal wiring is electrically interconnected with the bonding metal mini-pads (300-1) arranged on the hybrid bonding interface of the first wafer.

5. An array chip, comprising a plurality of SOC PMUTs suitable for high-density system integration according to claim 1, wherein the plurality of SOC PMUTs vertically connect the top metal layer (114) to the CMOS auxiliary circuit through the top metal link via ZTMs (163-1) respectively, then vertically connect to the second layer of metal (302) of the second wafer through the metal interconnection vias (312), then vertically connect to the second layer of metal wiring (202) of the first wafer through the bonding metal mini-pads (300-1, 300-2) arranged on the hybrid bonding interfaces of the two wafers, then vertically connect to the metal interconnect layer (201) of the CMOS unit through the two metal lead vias (212) respectively, and then lead to the back side of the silicon chip through the Through-Silicon Vias (TSVs) and connect to a printed circuit board (PCB) respectively.

6. A manufacturing method of the SOC PMUT suitable for high-density system integration according to claim 1, comprising the following steps:

step 1: preparing a first wafer, growing silicon dioxide on the surface of the first wafer, and manufacturing CMOS unit;

step 2: manufacturing PMUT unit on the CMOS unit and integrating CMOS auxiliary circuit, specifically comprising:

step 2-1: depositing a substrate material at a low temperature, and chemically and mechanically polishing the substrate material to form a flat surface of the substrate material;

step 2-2: performing photolithography and etching and metal deposition and filling to form metal lead vias between a metal interconnection layer and a second layer of metal wiring of the CMOS unit;

step 2-3: depositing a metal layer, performing photolithography and etching to form a second layer of metal wiring, removing a first photoresist and cleaning;

step 2-4: depositing a substrate material at a low temperature, and chemically and mechanically polishing the substrate material to form a flat surface of the substrate material;

step 2-5: performing photolithography and etching to form a cavity, removing a second photoresist and cleaning;

step 2-6: preparing a second wafer, growing silicon dioxide on the surface of the second wafer, manufacturing required CMOS auxiliary circuit, and bonding the second wafer to the first wafer;

step 2-7: grinding the back side of the second wafer, etching the back side with a chemical liquid, and reducing the thickness of the second wafer by chemical and mechanical polishing;

step 2-8: performing metal deposition to form a bottom metal layer;

step 2-9: depositing a piezoelectric material to form a piezoelectric material layer;

step 2-10: depositing a metal material on the top layer and performing photolithography and etching to form a top metal layer;

step 2-11: performing photolithography and etching, and metal deposition and filling to form metal link vias;

step 2-12: performing metal photolithography and etching to form required wiring;

step 3: performing photolithography and etching through the back side of the silicon substrate and performing metal deposition to form Through-Silicon Vias (TSVs).

7. The manufacturing method according to claim 6, wherein in the steps 2-6, after the silicon dioxide on the wafer surface is subjected to plasma treatment, the two wafers with performed CMOS structure are aligned face to face, pressurized and heated, and annealed, so as to form electrical connections between the bonding metal mini-pads on the hybrid bonding interfaces of the two wafers while the silicon dioxide are bonded together.

8. The manufacturing method according to claim 6, wherein the bottom metal layer employs a multi-layer structure with a lower layer formed by a titanium metal in thickness of 20 nm and an upper layer formed by a platinum material in thickness of 100 nm, wherein the titanium metal layer is formed by sputtering, while the platinum material layer is formed by evaporation in vacuum with an electron gun at heavy current and high temperature.

9. The manufacturing method according to claim 6, wherein the metal lead vias and the metal link vias are formed by sputtering titanium and depositing aluminum on a hot substrate or by sputtering titanium nitride and depositing aluminum on a hot substrate.

10. The manufacturing method according to claim 6, wherein in the steps 2-5, a cavity pattern is formed by photolithography first, and then the substrate material is etched with plasma chemical vapor to form a cavity in depth of 2 μm.

11. The manufacturing method according to claim 6, wherein the reduced thickness of the second wafer meets the design requirement for the thickness of the mechanical layer, and is usually 2 to 5 μm.

12. The manufacturing method according to claim 6, wherein before the two wafers are bonded together, bonding metal mini-pads (300-1) and bonding metal mini-pads (300-2) are arranged on the hybrid bonding interfaces of the first wafer and the second wafer respectively, the second layer of metal (302) is electrically interconnected with the bonding metal mini-pads (300-2) arranged on the hybrid bonding interface of the second wafer, and the second layer of metal wiring (202) is electrically interconnected with the bonding mini-pads (300-1) arranged on the hybrid bonding interface of the first wafer.

\* \* \* \* \*